(12) United States Patent
Reggiardo et al.

(10) Patent No.: US 8,344,966 B2
(45) Date of Patent: Jan. 1, 2013

(54) METHOD AND SYSTEM FOR PROVIDING A FAULT TOLERANT DISPLAY UNIT IN AN ELECTRONIC DEVICE

(75) Inventors: Christopher V. Reggiardo, Castro Valley, CA (US); Christopher L. Zeiger, Three Oaks, MI (US)

(73) Assignee: Abbott Diabetes Care Inc., Alameda, CA (US)

( * ) Notice: Subject to any disclaimer, the term of this patent is extended or adjusted under 35 U.S.C. 154(b) by 693 days.

(21) Appl. No.: 11/345,044

(22) Filed: Jan. 31, 2006

(65) Prior Publication Data

US 2007/0176867 A1 Aug. 2, 2007

(51) Int. Cl.
*G09G 3/36* (2006.01)

(52) U.S. Cl. .......................... 345/34; 345/33

(58) Field of Classification Search .......... 604/890.1, 604/131; 600/345, 310; 436/95; 345/33–34, 345/87

See application file for complete search history.

(56) References Cited

U.S. PATENT DOCUMENTS

| | | |
|---|---|---|
| 2,915,579 A | 12/1959 | Mendelsohn |
| 3,374,337 A | 3/1968 | Burley |
| 3,606,592 A | 9/1971 | Madurski et al. |
| 3,750,687 A | 8/1973 | Williams |
| 3,843,455 A | 10/1974 | Bier |
| 3,923,060 A | 12/1975 | Ellinwood |
| 3,930,493 A | 1/1976 | Williamson |
| 3,938,140 A * | 2/1976 | Garcia et al. ............ 345/50 |
| 3,994,799 A | 11/1976 | Yao et al. |
| 4,018,547 A | 4/1977 | Rogen |
| 4,121,282 A | 10/1978 | Ohsawa |
| 4,146,029 A | 3/1979 | Ellinwood |
| 4,193,397 A | 3/1980 | Tucker et al. |
| 4,268,173 A | 5/1981 | Barnard et al. |
| 4,288,793 A | 9/1981 | Lotscher |
| 4,362,052 A | 12/1982 | Heath et al. |
| 4,401,122 A | 8/1983 | Clark, Jr. |
| 4,439,197 A | 3/1984 | Honda et al. |
| 4,447,224 A | 5/1984 | DeCant, Jr. et al. |
| 4,458,686 A | 7/1984 | Clark, Jr. |

(Continued)

FOREIGN PATENT DOCUMENTS

EP 0455455 11/1991

(Continued)

OTHER PUBLICATIONS

International Preliminary Report on Patentability and Written Opinion of the International Searching Authority for PCT Application No. PCT/US2007/061072 filed Jan. 25, 2007 to Abbott Diabetes Care, Inc., mailed Aug. 14, 2008.

(Continued)

*Primary Examiner* — Quan-Zhen Wang
*Assistant Examiner* — Tony Davis
(74) *Attorney, Agent, or Firm* — Jackson & Co., LLP

(57) ABSTRACT

Method and apparatus for providing a fault tolerant display unit for an electronic device such as a glucose meter, including display unit, and a controller unit operatively coupled to the display unit, the controller unit configured to control the display unit to display an information, where when a failure mode of the display unit occurs, the display unit is configured to display a modified information, where the modified information is different from the information for display under the control of the controller unit, is provided.

27 Claims, 6 Drawing Sheets

U.S. PATENT DOCUMENTS

| | | |
|---|---|---|
| 4,467,811 A | 8/1984 | Clark, Jr. |
| 4,472,113 A | 9/1984 | Rogen |
| 4,494,950 A | 1/1985 | Fischell |
| 4,512,348 A | 4/1985 | Uchigaki et al. |
| 4,524,343 A | 6/1985 | Morgan et al. |
| 4,529,401 A | 7/1985 | Leslie et al. |
| 4,531,235 A | 7/1985 | Brusen |
| 4,562,751 A | 1/1986 | Nason et al. |
| 4,563,249 A | 1/1986 | Hale |
| 4,570,492 A | 2/1986 | Walsh |
| 4,573,994 A | 3/1986 | Fischell et al. |
| 4,633,878 A | 1/1987 | Bombardieri |
| 4,678,408 A | 7/1987 | Nason et al. |
| 4,685,903 A | 8/1987 | Cable et al. |
| 4,686,624 A | 8/1987 | Blum et al. |
| 4,736,748 A | 4/1988 | Nakamura et al. |
| 4,755,173 A | 7/1988 | Konopka et al. |
| 4,811,564 A | 3/1989 | Palmer |
| 4,850,959 A | 7/1989 | Findl |
| 4,851,827 A | 7/1989 | Nicholas |
| 4,866,396 A | 9/1989 | Tamura |
| 4,890,621 A | 1/1990 | Hakky |
| 4,953,552 A | 9/1990 | DeMarzo |
| 4,976,590 A | 12/1990 | Baldwin |
| 4,979,509 A | 12/1990 | Hakky |
| 4,984,581 A | 1/1991 | Stice |
| 5,004,532 A | 4/1991 | Hale et al. |
| 5,012,667 A | 5/1991 | Kruse |
| 5,019,974 A | 5/1991 | Beckers |
| 5,036,861 A | 8/1991 | Sembrowich et al. |
| 5,051,880 A | 9/1991 | Harm et al. |
| 5,061,914 A | 10/1991 | Busch et al. |
| 5,079,920 A | 1/1992 | Whitehead et al. |
| 5,081,421 A | 1/1992 | Miller et al. |
| 5,101,814 A | 4/1992 | Palti |
| 5,124,661 A | 6/1992 | Zelin et al. |
| 5,139,023 A | 8/1992 | Stanley et al. |
| 5,190,041 A | 3/1993 | Palti |
| 5,205,819 A | 4/1993 | Ross et al. |
| 5,207,666 A | 5/1993 | Idriss et al. |
| 5,211,371 A | 5/1993 | Coffee |
| 5,211,626 A | 5/1993 | Frank et al. |
| 5,262,305 A | 11/1993 | Heller et al. |
| 5,278,997 A | 1/1994 | Martin |
| 5,284,423 A | 2/1994 | Holdsworth et al. |
| 5,291,614 A | 3/1994 | Baker et al. |
| 5,291,887 A | 3/1994 | Stanley et al. |
| 5,324,599 A | 6/1994 | Oyama et al. |
| 5,325,280 A | 6/1994 | Tortola et al. |
| 5,349,852 A | 9/1994 | Kamen et al. |
| 5,356,786 A | 10/1994 | Heller et al. |
| 5,366,292 A | 11/1994 | Voss |
| 5,368,028 A | 11/1994 | Palti |
| 5,371,687 A | 12/1994 | Holmes, II et al. |
| 5,372,133 A | 12/1994 | Hogen Esch |
| 5,376,070 A | 12/1994 | Purvis et al. |
| 5,382,331 A | 1/1995 | Banks |
| 5,390,671 A | 2/1995 | Lord et al. |
| 5,391,250 A | 2/1995 | Cheney, II et al. |
| 5,398,681 A | 3/1995 | Kuperschmidt |
| 5,404,585 A | 4/1995 | Vimpari et al. |
| 5,406,301 A * | 4/1995 | Ravid ........................ 345/34 |
| 5,445,611 A | 8/1995 | Eppstein et al. |
| 5,448,992 A | 9/1995 | Kuperschmidt |
| 5,458,140 A | 10/1995 | Eppstein et al. |
| 5,469,025 A | 11/1995 | Kanemori et al. |
| 5,494,562 A | 2/1996 | Maley et al. |
| 5,497,772 A | 3/1996 | Schulman et al. |
| 5,505,713 A | 4/1996 | Van Antwerp |
| 5,507,288 A | 4/1996 | Bocker et al. |
| 5,515,390 A * | 5/1996 | Benton ........................ 714/811 |
| 5,517,434 A | 5/1996 | Hanson et al. |
| 5,526,844 A | 6/1996 | Kamen et al. |
| 5,533,389 A | 7/1996 | Kamen et al. |
| 5,543,678 A | 8/1996 | Hoiberg |
| 5,559,528 A * | 9/1996 | Ravid et al. ................. 345/618 |
| 5,568,400 A | 10/1996 | Stark et al. |
| 5,568,806 A | 10/1996 | Cheney, II et al. |
| 5,575,770 A | 11/1996 | Melsky et al. |
| 5,576,535 A | 11/1996 | Oosterwijk et al. |
| 5,586,553 A | 12/1996 | Halili et al. |
| 5,593,852 A | 1/1997 | Heller et al. |
| 5,594,906 A | 1/1997 | Holmes, II et al. |
| 5,601,435 A | 2/1997 | Quy |
| 5,604,404 A | 2/1997 | Sahara |
| 5,615,671 A | 4/1997 | Schoonen et al. |
| 5,622,413 A | 4/1997 | Kim et al. |
| 5,622,482 A | 4/1997 | Lee |
| 5,640,954 A | 6/1997 | Pfeiffer et al. |
| 5,645,709 A | 7/1997 | Birch et al. |
| 5,660,163 A | 8/1997 | Schulman et al. |
| 5,661,643 A | 8/1997 | Blakely et al. |
| 5,662,461 A | 9/1997 | Ono |
| 5,671,301 A | 9/1997 | Kuperschmidt |
| 5,695,949 A | 12/1997 | Galen et al. |
| 5,703,928 A | 12/1997 | Galloway et al. |
| 5,707,502 A | 1/1998 | McCaffrey et al. |
| 5,708,247 A | 1/1998 | McAleer et al. |
| 5,711,861 A | 1/1998 | Ward et al. |
| 5,711,868 A | 1/1998 | Maley et al. |
| 5,722,397 A | 3/1998 | Eppstein |
| 5,741,211 A | 4/1998 | Renirie et al. |
| 5,748,872 A | 5/1998 | Norman |
| 5,759,510 A | 6/1998 | Pillai |
| 5,771,890 A | 6/1998 | Tamada |
| 5,774,254 A | 6/1998 | Berlin |
| 5,786,439 A | 7/1998 | Van Antwerp et al. |
| 5,790,297 A | 8/1998 | Berlin |
| 5,791,344 A | 8/1998 | Schulman et al. |
| 5,812,102 A * | 9/1998 | Sprole et al. ................... 345/34 |
| 5,814,599 A | 9/1998 | Mitragotri et al. |
| 5,815,303 A | 9/1998 | Berlin |
| 5,822,715 A | 10/1998 | Worthington et al. |
| 5,825,488 A | 10/1998 | Kohl et al. |
| 5,848,990 A | 12/1998 | Cirelli et al. |
| 5,851,197 A | 12/1998 | Marano et al. |
| 5,873,026 A | 2/1999 | Reames |
| 5,885,211 A | 3/1999 | Eppstein et al. |
| 5,899,855 A | 5/1999 | Brown |
| 5,913,833 A | 6/1999 | Elstrom et al. |
| 5,918,603 A | 7/1999 | Brown |
| 5,923,512 A | 7/1999 | Brownlow et al. |
| 5,947,921 A | 9/1999 | Johnson et al. |
| 5,948,512 A | 9/1999 | Kubota et al. |
| 5,951,836 A | 9/1999 | McAleer et al. |
| 5,954,643 A | 9/1999 | Van Antwerp et al. |
| 5,965,380 A | 10/1999 | Heller et al. |
| 5,968,011 A | 10/1999 | Larsen et al. |
| 5,971,922 A | 10/1999 | Arita et al. |
| 6,001,067 A | 12/1999 | Shults et al. |
| 6,002,961 A | 12/1999 | Mitragotri et al. |
| 6,011,486 A | 1/2000 | Casey |
| 6,014,577 A | 1/2000 | Henning et al. |
| 6,017,328 A | 1/2000 | Fischell et al. |
| 6,018,678 A | 1/2000 | Mitragotri et al. |
| 6,023,629 A | 2/2000 | Tamada |
| 6,024,539 A | 2/2000 | Blomquist et al. |
| 6,026,320 A | 2/2000 | Carlson et al. |
| 6,027,459 A | 2/2000 | Shain et al. |
| 6,027,692 A | 2/2000 | Loomis et al. |
| 6,027,692 A | 2/2000 | Galen et al. |
| 6,032,059 A | 2/2000 | Henning et al. |
| 6,041,253 A | 3/2000 | Kost et al. |
| 6,041,665 A | 3/2000 | Hussain |
| 6,059,546 A | 5/2000 | Brenan et al. |
| 6,063,039 A | 5/2000 | Cunningham et al. |
| 6,064,368 A | 5/2000 | Kang |
| 6,066,243 A | 5/2000 | Anderson et al. |
| 6,067,017 A | 5/2000 | Stewart et al. |
| 6,067,463 A | 5/2000 | Jeng et al. |
| 6,071,249 A | 6/2000 | Cunningham et al. |
| 6,071,251 A | 6/2000 | Cunningham et al. |
| 6,073,031 A | 6/2000 | Helstab et al. |
| 6,077,660 A | 6/2000 | Wong et al. |
| 6,081,104 A | 6/2000 | Kern |
| 6,083,710 A | 7/2000 | Heller et al. |
| 6,085,871 A | 7/2000 | Karamata |

| | | |
|---|---|---|
| 6,086,575 A | 7/2000 | Mejslov |
| 6,091,975 A | 7/2000 | Daddona et al. |
| 6,093,156 A | 7/2000 | Cunningham et al. |
| 6,093,172 A | 7/2000 | Funderburk et al. |
| 6,121,009 A | 9/2000 | Heller et al. |
| 6,129,823 A | 10/2000 | Hughes et al. |
| 6,132,371 A | 10/2000 | Dempsey et al. |
| 6,142,939 A | 11/2000 | Eppstein et al. |
| 6,144,303 A | 11/2000 | Federman |
| 6,144,869 A | 11/2000 | Berner et al. |
| 6,144,922 A | 11/2000 | Douglas et al. |
| 6,147,342 A | 11/2000 | Kucher |
| 6,154,855 A | 11/2000 | Norman |
| 6,155,992 A | 12/2000 | Henning et al. |
| 6,157,442 A | 12/2000 | Raskas |
| 6,160,449 A | 12/2000 | Klomsdorf et al. |
| 6,162,202 A | 12/2000 | Sicurelli et al. |
| 6,162,611 A | 12/2000 | Heller et al. |
| 6,164,284 A | 12/2000 | Schulman et al. |
| 6,173,160 B1 | 1/2001 | Liimatainen |
| 6,175,752 B1 | 1/2001 | Say et al. |
| 6,180,416 B1 | 1/2001 | Kurnik et al. |
| 6,185,452 B1 | 2/2001 | Schulman et al. |
| 6,201,980 B1 | 3/2001 | Darrow et al. |
| 6,206,841 B1 | 3/2001 | Cunningham et al. |
| 6,208,894 B1 | 3/2001 | Schulman et al. |
| 6,212,416 B1 | 4/2001 | Ward et al. |
| 6,215,206 B1 | 4/2001 | Chitayat |
| 6,222,514 B1 | 4/2001 | DeLuca |
| 6,232,370 B1 | 5/2001 | Kubota et al. |
| 6,233,471 B1 | 5/2001 | Berner et al. |
| 6,233,539 B1 | 5/2001 | Brown |
| 6,242,961 B1 | 6/2001 | Liu et al. |
| 6,245,060 B1 | 6/2001 | Loomis et al. |
| 6,248,067 B1 | 6/2001 | Causey, III et al. |
| 6,262,708 B1 | 7/2001 | Chu |
| 6,272,364 B1 | 8/2001 | Kurnik |
| 6,278,425 B1 | 8/2001 | DeLuca |
| 6,280,587 B1 | 8/2001 | Matsumoto |
| 6,283,926 B1 | 9/2001 | Cunningham et al. |
| 6,284,478 B1 | 9/2001 | Heller et al. |
| 6,288,653 B1 | 9/2001 | Shih |
| 6,293,925 B1 | 9/2001 | Safabash et al. |
| 6,295,506 B1 | 9/2001 | Heinonen et al. |
| 6,298,254 B2 | 10/2001 | Tamada |
| 6,298,255 B1 | 10/2001 | Cordero et al. |
| 6,299,578 B1 | 10/2001 | Kurnik et al. |
| 6,301,499 B1 | 10/2001 | Carlson et al. |
| 6,306,104 B1 | 10/2001 | Cunningham et al. |
| 6,309,351 B1 | 10/2001 | Kurnik et al. |
| 6,312,888 B1 | 11/2001 | Wong et al. |
| 6,315,721 B2 | 11/2001 | Schulman et al. |
| 6,326,160 B1 | 12/2001 | Dunn et al. |
| 6,329,161 B1 | 12/2001 | Heller et al. |
| 6,341,232 B1 | 1/2002 | Conn et al. |
| 6,356,776 B1 | 3/2002 | Berner et al. |
| 6,360,888 B1 | 3/2002 | McIvor et al. |
| 6,366,793 B1 | 4/2002 | Bell et al. |
| 6,368,141 B1 | 4/2002 | Van Antwerp et al. |
| 6,368,274 B1 | 4/2002 | Van Antwerp et al. |
| 6,372,371 B1 | 4/2002 | Iarochenko et al. |
| 6,375,344 B1 | 4/2002 | Hanson et al. |
| 6,375,638 B2 | 4/2002 | Nason et al. |
| 6,377,894 B1 | 4/2002 | Deweese et al. |
| 6,379,301 B1 | 4/2002 | Worthington et al. |
| 6,381,496 B1 | 4/2002 | Meadows et al. |
| 6,393,318 B1 | 5/2002 | Conn et al. |
| 6,403,944 B1 | 6/2002 | MacKenzie et al. |
| 6,405,066 B1 | 6/2002 | Essenpreis et al. |
| 6,408,402 B1 | 6/2002 | Norman |
| 6,417,074 B2 | 7/2002 | Kopley et al. |
| 6,419,642 B1 | 7/2002 | Marchitto et al. |
| 6,425,829 B1 | 7/2002 | Julien |
| 6,427,088 B1 | 7/2002 | Bowman, IV et al. |
| 6,432,585 B1 | 8/2002 | Kawakami et al. |
| 6,437,379 B2 | 8/2002 | Kopley et al. |
| 6,438,385 B1 | 8/2002 | Heinonen et al. |
| 6,438,414 B1 | 8/2002 | Conn et al. |
| 6,442,413 B1 | 8/2002 | Silver |
| 6,461,329 B1 | 10/2002 | Van Antwerp et al. |
| 6,462,162 B2 | 10/2002 | Van Antwerp et al. |
| 6,464,848 B1 | 10/2002 | Matsumoto |
| 6,466,807 B1 | 10/2002 | Dobson et al. |
| 6,466,810 B1 | 10/2002 | Ward et al. |
| 6,468,222 B1 | 10/2002 | Mault et al. |
| 6,471,980 B2 | 10/2002 | Sirhan et al. |
| 6,472,991 B1 | 10/2002 | Schulman et al. |
| 6,475,196 B1 | 11/2002 | Vachon |
| 6,478,736 B1 | 11/2002 | Mault |
| 6,480,730 B2 | 11/2002 | Darrow et al. |
| 6,482,158 B2 | 11/2002 | Mault |
| 6,484,045 B1 | 11/2002 | Holker et al. |
| 6,485,138 B1 | 11/2002 | Kubota et al. |
| 6,485,461 B1 | 11/2002 | Mason et al. |
| 6,492,180 B2 | 12/2002 | Brown et al. |
| 6,506,168 B1 | 1/2003 | Fathallah et al. |
| 6,513,532 B2 | 2/2003 | Mault et al. |
| 6,514,460 B1 | 2/2003 | Fendrock |
| 6,514,689 B2 | 2/2003 | Han et al. |
| 6,514,718 B2 | 2/2003 | Heller et al. |
| 6,522,530 B2 | 2/2003 | Bang |
| 6,525,330 B2 | 2/2003 | Paolini et al. |
| 6,526,298 B1 | 2/2003 | Khalil et al. |
| 6,529,772 B2 | 3/2003 | Carlson et al. |
| 6,530,915 B1 | 3/2003 | Eppstein et al. |
| 6,535,753 B1 | 3/2003 | Raskas |
| 6,537,243 B1 | 3/2003 | Henning et al. |
| 6,540,675 B2 | 4/2003 | Aceti et al. |
| 6,540,891 B1 | 4/2003 | Stewart et al. |
| 6,544,212 B2 | 4/2003 | Galley et al. |
| 6,546,269 B1 | 4/2003 | Kurnik |
| 6,549,796 B2 | 4/2003 | Sohrab |
| 6,551,276 B1 | 4/2003 | Mann et al. |
| 6,554,798 B1 | 4/2003 | Mann et al. |
| 6,558,320 B1 | 5/2003 | Causey, III et al. |
| 6,558,321 B1 | 5/2003 | Burd et al. |
| 6,558,351 B1 * | 5/2003 | Steil et al. .................. 604/131 |
| 6,560,471 B1 | 5/2003 | Heller et al. |
| 6,561,978 B1 | 5/2003 | Conn et al. |
| 6,562,001 B2 | 5/2003 | Lebel et al. |
| 6,564,105 B2 | 5/2003 | Starkweather et al. |
| 6,564,807 B1 | 5/2003 | Schulman et al. |
| 6,565,509 B1 | 5/2003 | Say et al. |
| 6,565,738 B1 | 5/2003 | Henning et al. |
| 6,569,157 B1 | 5/2003 | Shain et al. |
| 6,571,128 B2 | 5/2003 | Lebel et al. |
| 6,571,200 B1 | 5/2003 | Mault |
| 6,576,117 B1 | 6/2003 | Iketaki et al. |
| 6,577,899 B2 | 6/2003 | Lebel et al. |
| 6,579,498 B1 | 6/2003 | Eglise |
| 6,579,690 B1 | 6/2003 | Bonnecaze et al. |
| 6,582,393 B2 | 6/2003 | Sage, Jr. |
| 6,585,644 B2 | 7/2003 | Lebel et al. |
| 6,586,971 B1 | 7/2003 | Naffziger et al. |
| 6,587,705 B1 | 7/2003 | Berner et al. |
| 6,589,229 B1 * | 7/2003 | Connelly et al. ........... 604/890.1 |
| 6,594,514 B2 | 7/2003 | Berner et al. |
| 6,595,919 B2 | 7/2003 | Berner et al. |
| 6,596,016 B1 | 7/2003 | Vreman et al. |
| 6,600,997 B2 | 7/2003 | Deweese et al. |
| 6,602,469 B1 | 8/2003 | Maus et al. |
| 6,607,509 B2 | 8/2003 | Bobroff et al. |
| 6,610,012 B2 | 8/2003 | Mault |
| 6,612,306 B1 | 9/2003 | Mault |
| 6,615,061 B1 | 9/2003 | Khalil et al. |
| 6,615,074 B2 | 9/2003 | Mickle et al. |
| 6,618,603 B2 | 9/2003 | Varalli et al. |
| 6,620,106 B2 | 9/2003 | Mault |
| 6,629,934 B2 | 10/2003 | Mault et al. |
| 6,633,095 B1 | 10/2003 | Swope et al. |
| 6,633,772 B2 | 10/2003 | Ford et al. |
| 6,635,014 B2 | 10/2003 | Starkweather et al. |
| 6,641,533 B2 | 11/2003 | Causey, III et al. |
| 6,645,142 B2 | 11/2003 | Braig et al. |
| 6,648,821 B2 | 11/2003 | Lebel et al. |
| 6,650,064 B2 | 11/2003 | Guthrie et al. |
| 6,653,091 B1 | 11/2003 | Dunn et al. |
| 6,656,158 B2 | 12/2003 | Mahoney et al. |

| Patent No. | Date | Inventor |
|---|---|---|
| 6,656,159 B2 | 12/2003 | Flaherty |
| 6,659,948 B2 | 12/2003 | Lebel et al. |
| 6,668,196 B1 | 12/2003 | Villegas et al. |
| 6,669,663 B1 | 12/2003 | Thompson |
| 6,669,669 B2 | 12/2003 | Flaherty et al. |
| 6,670,806 B2 | 12/2003 | Wendt et al. |
| 6,679,841 B2 | 1/2004 | Bojan et al. |
| 6,687,522 B2 | 2/2004 | Tamada |
| 6,687,546 B2 | 2/2004 | Lebel et al. |
| 6,692,457 B2 | 2/2004 | Flaherty |
| 6,694,191 B2 | 2/2004 | Lebel et al. |
| 6,695,885 B2 | 2/2004 | Schulman et al. |
| 6,699,218 B2 | 3/2004 | Flaherty et al. |
| 6,702,857 B2 | 3/2004 | Brauker et al. |
| 6,723,072 B2 | 4/2004 | Flaherty et al. |
| 6,728,560 B2 | 4/2004 | Kollias et al. |
| 6,730,200 B1 | 5/2004 | Stewart et al. |
| 6,731,976 B2 | 5/2004 | Penn et al. |
| 6,733,446 B2 | 5/2004 | Lebel et al. |
| 6,736,777 B2 | 5/2004 | Kim et al. |
| 6,736,797 B1 | 5/2004 | Larsen et al. |
| 6,738,654 B2 | 5/2004 | Sohrab |
| 6,740,059 B2 | 5/2004 | Flaherty |
| 6,740,075 B2 | 5/2004 | Lebel et al. |
| 6,741,877 B1 | 5/2004 | Shults et al. |
| 6,743,635 B2 * | 6/2004 | Neel et al. .................. 436/95 |
| 6,749,587 B2 | 6/2004 | Flaherty |
| 6,752,787 B1 | 6/2004 | Causey, III et al. |
| 6,758,810 B2 | 7/2004 | Lebel et al. |
| 6,764,581 B1 | 7/2004 | Forrow et al. |
| 6,768,425 B2 | 7/2004 | Flaherty et al. |
| 6,770,030 B1 | 8/2004 | Schaupp et al. |
| 6,770,729 B2 | 8/2004 | Van Antwerp |
| 6,773,563 B2 | 8/2004 | Matsumoto |
| 6,779,984 B2 | 8/2004 | Lilie et al. |
| 6,790,178 B1 | 9/2004 | Mault et al. |
| 6,794,195 B2 | 9/2004 | Colvin, Jr. |
| 6,799,861 B2 | 10/2004 | Naghi et al. |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,816,742 B2 | 11/2004 | Kim et al. |
| 6,818,348 B1 | 11/2004 | Venkatesan et al. |
| 6,830,558 B2 | 12/2004 | Flaherty et al. |
| 6,832,114 B1 | 12/2004 | Whitehurst et al. |
| 6,833,540 B2 | 12/2004 | MacKenzie et al. |
| 6,835,553 B2 | 12/2004 | Han et al. |
| 6,837,858 B2 | 1/2005 | Cunningham et al. |
| 6,839,596 B2 | 1/2005 | Nelson et al. |
| 6,840,912 B2 | 1/2005 | Kloepfer et al. |
| 6,849,237 B2 | 2/2005 | Housefield et al. |
| 6,850,790 B2 | 2/2005 | Berner et al. |
| 6,859,831 B1 | 2/2005 | Gelvin et al. |
| 6,862,465 B2 | 3/2005 | Shults et al. |
| 6,872,200 B2 | 3/2005 | Mann et al. |
| 6,873,268 B2 | 3/2005 | Lebel et al. |
| 6,881,551 B2 | 4/2005 | Heller et al. |
| 6,892,085 B2 | 5/2005 | McIvor et al. |
| 6,893,396 B2 | 5/2005 | Schulze et al. |
| 6,895,265 B2 | 5/2005 | Silver |
| 6,898,451 B2 | 5/2005 | Wuori |
| 6,899,683 B2 | 5/2005 | Mault et al. |
| 6,899,684 B2 | 5/2005 | Mault et al. |
| 6,904,301 B2 | 6/2005 | Raskas |
| 6,907,127 B1 | 6/2005 | Kravitz et al. |
| 6,908,535 B2 | 6/2005 | Rankin et al. |
| 6,916,159 B2 | 7/2005 | Rush et al. |
| 6,918,874 B1 | 7/2005 | Hatch et al. |
| 6,922,576 B2 | 7/2005 | Raskas |
| 6,922,578 B2 | 7/2005 | Eppstein et al. |
| 6,923,764 B2 | 8/2005 | Aceti et al. |
| 6,927,749 B1 * | 8/2005 | Klemm ................ 345/33 |
| 6,931,327 B2 | 8/2005 | Goode, Jr. et al. |
| 6,936,029 B2 | 8/2005 | Mann et al. |
| 6,949,816 B2 | 9/2005 | Brown et al. |
| 6,950,708 B2 | 9/2005 | Bowman IV et al. |
| 6,952,603 B2 | 10/2005 | Gerber et al. |
| 6,955,650 B2 | 10/2005 | Mault et al. |
| 6,958,129 B2 | 10/2005 | Galen et al. |
| 6,958,705 B2 | 10/2005 | Lebel et al. |
| 6,960,192 B1 | 11/2005 | Flaherty et al. |
| 6,974,437 B2 | 12/2005 | Lebel et al. |
| 6,979,326 B2 | 12/2005 | Mann et al. |
| 6,990,366 B2 | 1/2006 | Say et al. |
| 6,990,372 B2 | 1/2006 | Perron et al. |
| 6,997,911 B2 | 2/2006 | Klitmose |
| 6,997,920 B2 | 2/2006 | Mann et al. |
| 6,999,810 B2 | 2/2006 | Berner et al. |
| 7,003,340 B2 | 2/2006 | Say et al. |
| 7,003,341 B2 | 2/2006 | Say et al. |
| 7,005,857 B2 | 2/2006 | Stiene et al. |
| 7,006,858 B2 | 2/2006 | Silver et al. |
| 7,010,356 B2 | 3/2006 | Jog et al. |
| 7,011,630 B2 | 3/2006 | Desai et al. |
| 7,018,360 B2 | 3/2006 | Flaherty et al. |
| 7,020,508 B2 | 3/2006 | Stivoric et al. |
| 7,024,245 B2 | 4/2006 | Lebel et al. |
| 7,024,249 B2 | 4/2006 | Weisner et al. |
| 7,025,743 B2 | 4/2006 | Mann et al. |
| 7,029,444 B2 | 4/2006 | Shin et al. |
| 7,029,455 B2 | 4/2006 | Flaherty |
| 7,034,677 B2 | 4/2006 | Steinthal et al. |
| 7,041,468 B2 | 5/2006 | Drucker et al. |
| 7,043,287 B1 | 5/2006 | Khalil et al. |
| 7,052,251 B2 | 5/2006 | Nason et al. |
| 7,067,498 B2 | 6/2006 | Wolf et al. |
| 7,070,591 B2 | 7/2006 | Adams et al. |
| 7,072,738 B2 | 7/2006 | Bonney et al. |
| 7,074,307 B2 | 7/2006 | Simpson et al. |
| 7,077,328 B2 | 7/2006 | Krishnaswamy et al. |
| 7,079,901 B1 | 7/2006 | Loftin et al. |
| 7,081,195 B2 | 7/2006 | Simpson et al. |
| 7,083,593 B2 | 8/2006 | Stultz |
| 7,086,277 B2 | 8/2006 | Tess et al. |
| 7,092,762 B1 | 8/2006 | Loftin et al. |
| 7,097,983 B2 | 8/2006 | Markovsky et al. |
| 7,098,803 B2 | 8/2006 | Mann et al. |
| 7,108,711 B2 | 9/2006 | Vogel et al. |
| 7,108,778 B2 | 9/2006 | Simpson et al. |
| 7,110,803 B2 | 9/2006 | Shults et al. |
| 7,114,502 B2 | 10/2006 | Schulman et al. |
| 7,123,206 B2 | 10/2006 | Hess et al. |
| 7,133,710 B2 | 11/2006 | Acosta et al. |
| 7,134,999 B2 | 11/2006 | Brauker et al. |
| 7,136,689 B2 | 11/2006 | Shults et al. |
| 7,136,704 B2 | 11/2006 | Schulman |
| 7,137,964 B2 | 11/2006 | Flaherty |
| 7,144,384 B2 | 12/2006 | Gorman et al. |
| 7,149,581 B2 | 12/2006 | Goedeke |
| 7,153,212 B1 | 12/2006 | Karten et al. |
| 7,154,398 B2 | 12/2006 | Chen et al. |
| 7,163,511 B2 | 1/2007 | Conn et al. |
| 7,167,818 B2 | 1/2007 | Brown |
| 7,171,274 B2 | 1/2007 | Starkweather et al. |
| 7,181,261 B2 | 2/2007 | Silver et al. |
| 7,186,566 B2 | 3/2007 | Qian |
| 7,186,791 B2 | 3/2007 | Bruno et al. |
| 7,192,450 B2 | 3/2007 | Brauker et al. |
| 7,198,603 B2 | 4/2007 | Penner et al. |
| 7,202,734 B1 | 4/2007 | Raab |
| 7,205,409 B2 | 4/2007 | Pei et al. |
| 7,208,119 B1 | 4/2007 | Kurtock et al. |
| 7,211,048 B1 | 5/2007 | Najafi et |
| 7,218,017 B1 | 5/2007 | Chitayat et al. |
| 7,225,535 B2 | 6/2007 | Feldman et al. |
| 7,226,278 B2 | 6/2007 | Nason et al. |
| 7,226,442 B2 | 6/2007 | Sheppard, Jr. et al. |
| 7,226,978 B2 | 6/2007 | Tapsak et al. |
| 7,258,666 B2 | 8/2007 | Brown |
| 7,266,400 B2 | 9/2007 | Fine et al. |
| 7,276,029 B2 | 10/2007 | Goode, Jr. et al. |
| 7,283,867 B2 | 10/2007 | Strother et al. |
| 7,299,080 B2 | 11/2007 | Acosta et al. |
| 7,303,549 B2 | 12/2007 | Flaherty et al. |
| 7,310,544 B2 * | 12/2007 | Brister et al. ................ 600/345 |
| 7,323,091 B1 | 1/2008 | Gillette et al. |

| | | |
|---|---|---|
| 7,324,949 B2 | 1/2008 | Bristol et al. |
| 7,364,592 B2 | 4/2008 | Carr-Brendel et al. |
| 7,366,556 B2 | 4/2008 | Brister et al. |
| 7,379,765 B2 | 5/2008 | Petisce et al. |
| 7,424,318 B2 | 9/2008 | Brister et al. |
| 7,460,898 B2 | 12/2008 | Brister et al. |
| 7,467,003 B2 | 12/2008 | Brister et al. |
| 7,471,972 B2 | 12/2008 | Rhodes et al. |
| 7,480,138 B2 | 1/2009 | Kogan et al. |
| 7,494,465 B2 | 2/2009 | Brister et al. |
| 7,497,827 B2 | 3/2009 | Brister et al. |
| 7,510,526 B2 | 3/2009 | Merry et al. |
| 7,519,408 B2 | 4/2009 | Rasdal et al. |
| 7,583,190 B2 | 9/2009 | Reggiardo et al. |
| 7,583,990 B2 | 9/2009 | Goode, Jr. et al. |
| 7,591,801 B2 | 9/2009 | Brauker et al. |
| 7,599,726 B2 | 10/2009 | Goode, Jr. et al. |
| 7,602,310 B2 | 10/2009 | Mann et al. |
| 7,613,491 B2 | 11/2009 | Boock et al. |
| 7,615,007 B2 | 11/2009 | Shults et al. |
| 7,620,437 B2 | 11/2009 | Reggiardo |
| 7,632,228 B2 | 12/2009 | Brauker et al. |
| 7,637,868 B2 | 12/2009 | Saint et al. |
| 7,640,048 B2 | 12/2009 | Dobbles et al. |
| 7,651,596 B2 | 1/2010 | Petisce et al. |
| 7,654,956 B2 | 2/2010 | Brister et al. |
| 7,657,297 B2 | 2/2010 | Simpson et al. |
| 7,711,402 B2 | 5/2010 | Shults et al. |
| 7,713,574 B2 | 5/2010 | Brister et al. |
| 7,715,893 B2 | 5/2010 | Kamath et al. |
| 2001/0016682 A1 | 8/2001 | Berner et al. |
| 2001/0016683 A1 | 8/2001 | Darrow et al. |
| 2001/0016710 A1 | 8/2001 | Nason et al. |
| 2001/0020124 A1 | 9/2001 | Tamada |
| 2001/0023095 A1 | 9/2001 | Kopley et al. |
| 2001/0024864 A1 | 9/2001 | Kopley et al. |
| 2001/0029340 A1 | 10/2001 | Mault et al. |
| 2001/0034502 A1 | 10/2001 | Moberg et al. |
| 2001/0037060 A1 | 11/2001 | Thompson et al. |
| 2001/0037069 A1 | 11/2001 | Carlson et al. |
| 2001/0041830 A1 | 11/2001 | Varalli et al. |
| 2001/0044581 A1 | 11/2001 | Mault |
| 2001/0044588 A1 | 11/2001 | Mault |
| 2001/0049470 A1 | 12/2001 | Mault et al. |
| 2001/0053891 A1 | 12/2001 | Ackley |
| 2001/0056255 A1 | 12/2001 | Kost et al. |
| 2002/0002326 A1 | 1/2002 | Causey, III et al. |
| 2002/0002328 A1 | 1/2002 | Tamada |
| 2002/0004640 A1 | 1/2002 | Conn et al. |
| 2002/0010414 A1 | 1/2002 | Coston et al. |
| 2002/0019022 A1 | 2/2002 | Dunn et al. |
| 2002/0019612 A1* | 2/2002 | Watanabe et al. ............. 604/246 |
| 2002/0026937 A1 | 3/2002 | Mault |
| 2002/0027164 A1 | 3/2002 | Mault et al. |
| 2002/0028995 A1 | 3/2002 | Mault |
| 2002/0032374 A1 | 3/2002 | Holker et al. |
| 2002/0040208 A1 | 4/2002 | Flaherty et al. |
| 2002/0042090 A1 | 4/2002 | Heller et al. |
| 2002/0047867 A1 | 4/2002 | Mault et al. |
| 2002/0053637 A1 | 5/2002 | Conn et al. |
| 2002/0062069 A1 | 5/2002 | Mault |
| 2002/0068858 A1 | 6/2002 | Braig et al. |
| 2002/0077765 A1 | 6/2002 | Mault |
| 2002/0077766 A1 | 6/2002 | Mault |
| 2002/0087056 A1 | 7/2002 | Aceti et al. |
| 2002/0091312 A1 | 7/2002 | Berner et al. |
| 2002/0091454 A1 | 7/2002 | Vasko |
| 2002/0103425 A1 | 8/2002 | Mault |
| 2002/0107433 A1 | 8/2002 | Mault |
| 2002/0107476 A1 | 8/2002 | Mann et al. |
| 2002/0109600 A1 | 8/2002 | Mault et al. |
| 2002/0118090 A1 | 8/2002 | Park et al. |
| 2002/0119711 A1 | 8/2002 | Van Antwerp et al. |
| 2002/0124017 A1 | 9/2002 | Mault |
| 2002/0133378 A1 | 9/2002 | Mault et al. |
| 2002/0161286 A1 | 10/2002 | Gerber et al. |
| 2002/0169394 A1 | 11/2002 | Eppstein et al. |
| 2002/0177764 A1 | 11/2002 | Sohrab |
| 2002/0193679 A1 | 12/2002 | Malave et al. |
| 2003/0009133 A1 | 1/2003 | Ramey |
| 2003/0023182 A1 | 1/2003 | Mault et al. |
| 2003/0023317 A1 | 1/2003 | Brauker et al. |
| 2003/0028089 A1 | 2/2003 | Galley et al. |
| 2003/0028120 A1 | 2/2003 | Mault et al. |
| 2003/0032868 A1 | 2/2003 | Graskov et al. |
| 2003/0032874 A1 | 2/2003 | Rhodes et al. |
| 2003/0040683 A1 | 2/2003 | Rule et al. |
| 2003/0050546 A1 | 3/2003 | Desai et al. |
| 2003/0050575 A1 | 3/2003 | Diermann et al. |
| 2003/0060692 A1* | 3/2003 | Ruchti et al. ................. 600/310 |
| 2003/0060765 A1 | 3/2003 | Campbell et al. |
| 2003/0065257 A1 | 4/2003 | Mault et al. |
| 2003/0065273 A1 | 4/2003 | Mault et al. |
| 2003/0065274 A1 | 4/2003 | Mault et al. |
| 2003/0065275 A1 | 4/2003 | Mault et al. |
| 2003/0065308 A1 | 4/2003 | Lebel et al. |
| 2003/0078560 A1 | 4/2003 | Miller et al. |
| 2003/0100040 A1 | 5/2003 | Bonnecaze et al. |
| 2003/0100821 A1 | 5/2003 | Heller et al. |
| 2003/0105407 A1 | 6/2003 | Pearce, Jr. et al. |
| 2003/0107487 A1 | 6/2003 | Korman et al. |
| 2003/0108976 A1 | 6/2003 | Braig et al. |
| 2003/0118460 A1 | 6/2003 | Lilie et al. |
| 2003/0130616 A1 | 7/2003 | Steil et al. |
| 2003/0134347 A1 | 7/2003 | Heller et al. |
| 2003/0135100 A1 | 7/2003 | Kim et al. |
| 2003/0135333 A1 | 7/2003 | Aceti et al. |
| 2003/0153820 A1 | 8/2003 | Berner et al. |
| 2003/0153821 A1 | 8/2003 | Berner et al. |
| 2003/0158472 A1 | 8/2003 | Sohrab |
| 2003/0158707 A1 | 8/2003 | Doi |
| 2003/0175806 A1 | 9/2003 | Rule et al. |
| 2003/0176933 A1 | 9/2003 | Lebel et al. |
| 2003/0181851 A1 | 9/2003 | Mann et al. |
| 2003/0181852 A1 | 9/2003 | Mann et al. |
| 2003/0187338 A1 | 10/2003 | Say et al. |
| 2003/0187525 A1 | 10/2003 | Mann et al. |
| 2003/0191376 A1 | 10/2003 | Samuels et al. |
| 2003/0191431 A1 | 10/2003 | Mann et al. |
| 2003/0195403 A1 | 10/2003 | Berner et al. |
| 2003/0195462 A1 | 10/2003 | Mann et al. |
| 2003/0198558 A1 | 10/2003 | Nason et al. |
| 2003/0199825 A1 | 10/2003 | Flaherty |
| 2003/0199837 A1 | 10/2003 | Vachon |
| 2003/0208110 A1 | 11/2003 | Mault et al. |
| 2003/0208113 A1 | 11/2003 | Mault et al. |
| 2003/0208133 A1 | 11/2003 | Mault |
| 2003/0208154 A1 | 11/2003 | Close et al. |
| 2003/0208409 A1 | 11/2003 | Mault |
| 2003/0212346 A1 | 11/2003 | Yuzhakov et al. |
| 2003/0212364 A1 | 11/2003 | Mann et al. |
| 2003/0212379 A1 | 11/2003 | Bylund et al. |
| 2003/0217966 A1 | 11/2003 | Tapsak et al. |
| 2003/0225360 A1 | 12/2003 | Eppstein et al. |
| 2003/0225361 A1 | 12/2003 | Sabra |
| 2003/0226695 A1 | 12/2003 | Mault |
| 2003/0232370 A1 | 12/2003 | Trifiro |
| 2003/0235817 A1 | 12/2003 | Bartkowiak et al. |
| 2004/0011671 A1 | 1/2004 | Shults et al. |
| 2004/0018486 A1 | 1/2004 | Dunn et al. |
| 2004/0019321 A1 | 1/2004 | Sage et al. |
| 2004/0027253 A1* | 2/2004 | Marsh et al. ............. 340/870.02 |
| 2004/0039256 A1 | 2/2004 | Kawatahara et al. |
| 2004/0041749 A1* | 3/2004 | Dixon ............................ 345/33 |
| 2004/0045879 A1 | 3/2004 | Shults et al. |
| 2004/0054263 A1 | 3/2004 | Moerman et al. |
| 2004/0059201 A1 | 3/2004 | Ginsberg |
| 2004/0064133 A1 | 4/2004 | Miller et al. |
| 2004/0072357 A1 | 4/2004 | Stiene et al. |
| 2004/0073095 A1 | 4/2004 | Causey, III et al. |
| 2004/0085215 A1 | 5/2004 | Moberg et al. |
| 2004/0096959 A1 | 5/2004 | Stiene et al. |
| 2004/0100376 A1 | 5/2004 | Lye et al. |
| 2004/0106858 A1 | 6/2004 | Say et al. |
| 2004/0106859 A1 | 6/2004 | Say et al. |
| 2004/0106860 A1 | 6/2004 | Say et al. |
| 2004/0108226 A1 | 6/2004 | Polychronakos et al. |
| 2004/0115067 A1 | 6/2004 | Rush et al. |

| | | |
|---|---|---|
| 2004/0122353 A1 | 6/2004 | Shahmirian et al. |
| 2004/0132220 A1 | 7/2004 | Fish |
| 2004/0133092 A1 | 7/2004 | Kain |
| 2004/0152622 A1 | 8/2004 | Keith et al. |
| 2004/0158137 A1 | 8/2004 | Eppstein et al. |
| 2004/0162473 A1 | 8/2004 | Sohrab |
| 2004/0164961 A1 | 8/2004 | Bal et al. |
| 2004/0167383 A1 | 8/2004 | Kim et al. |
| 2004/0167801 A1 | 8/2004 | Say et al. |
| 2004/0171921 A1 | 9/2004 | Say et al. |
| 2004/0176913 A1 | 9/2004 | Kawatahara et al. |
| 2004/0186362 A1 | 9/2004 | Brauker et al. |
| 2004/0186365 A1 | 9/2004 | Jin et al. |
| 2004/0193025 A1 | 9/2004 | Steil et al. |
| 2004/0193090 A1 | 9/2004 | Lebel et al. |
| 2004/0199059 A1 | 10/2004 | Brauker et al. |
| 2004/0202576 A1 | 10/2004 | Aceti et al. |
| 2004/0207054 A1 | 10/2004 | Brown et al. |
| 2004/0208780 A1 | 10/2004 | Faries, Jr. et al. |
| 2004/0210184 A1 | 10/2004 | Kost et al. |
| 2004/0225338 A1 | 11/2004 | Lebel et al. |
| 2004/0236200 A1 | 11/2004 | Say et al. |
| 2004/0248204 A1 | 12/2004 | Moerman |
| 2004/0249250 A1 | 12/2004 | McGee et al. |
| 2004/0249253 A1 | 12/2004 | Racchini et al. |
| 2004/0249254 A1 | 12/2004 | Racchini et al. |
| 2004/0249999 A1 | 12/2004 | Connolly et al. |
| 2004/0253736 A1 | 12/2004 | Stout et al. |
| 2004/0254429 A1 | 12/2004 | Yang |
| 2004/0254434 A1 | 12/2004 | Goodnow et al. |
| 2004/0263354 A1 | 12/2004 | Mann et al. |
| 2005/0003470 A1 | 1/2005 | Nelson et al. |
| 2005/0009126 A1 | 1/2005 | Andrews et al. |
| 2005/0010269 A1 | 1/2005 | Lebel et al. |
| 2005/0016276 A1 | 1/2005 | Guan et al. |
| 2005/0027179 A1 | 2/2005 | Berner et al. |
| 2005/0027180 A1 | 2/2005 | Goode, Jr. et al. |
| 2005/0027181 A1 | 2/2005 | Goode, Jr. et al. |
| 2005/0027462 A1 | 2/2005 | Goode, Jr. et al. |
| 2005/0027463 A1 | 2/2005 | Goode, Jr. et al. |
| 2005/0031689 A1 | 2/2005 | Shults et al. |
| 2005/0033132 A1 | 2/2005 | Shults et al. |
| 2005/0038680 A1 | 2/2005 | McMahon |
| 2005/0043598 A1 | 2/2005 | Goode, Jr. et al. |
| 2005/0043894 A1 | 2/2005 | Fernandez |
| 2005/0045476 A1 | 3/2005 | Neel et al. |
| 2005/0049473 A1 | 3/2005 | Desai et al. |
| 2005/0051580 A1 | 3/2005 | Ramey |
| 2005/0053365 A1 | 3/2005 | Adams et al. |
| 2005/0054909 A1 | 3/2005 | Petisce et al. |
| 2005/0059926 A1 | 3/2005 | Sage, Jr. et al. |
| 2005/0065464 A1 | 3/2005 | Talbot et al. |
| 2005/0090607 A1 | 4/2005 | Tapsak et al. |
| 2005/0090808 A1* | 4/2005 | Malave et al. .............. 604/890.1 |
| 2005/0112169 A1 | 5/2005 | Brauker et al. |
| 2005/0113657 A1 | 5/2005 | Alarcon et al. |
| 2005/0113658 A1 | 5/2005 | Jacobson et al. |
| 2005/0118726 A1 | 6/2005 | Scultz et al. |
| 2005/0121322 A1 | 6/2005 | Say et al. |
| 2005/0124873 A1 | 6/2005 | Shults et al. |
| 2005/0137471 A1 | 6/2005 | Haar et al. |
| 2005/0143635 A1 | 6/2005 | Kamath |
| 2005/0143636 A1 | 6/2005 | Zhang et al. |
| 2005/0148003 A1 | 7/2005 | Keith et al. |
| 2005/0154271 A1 | 7/2005 | Rasdal et al. |
| 2005/0161346 A1 | 7/2005 | Simpson et al. |
| 2005/0171503 A1 | 8/2005 | Van Den Berghe et al. |
| 2005/0171512 A1 | 8/2005 | Flaherty |
| 2005/0171513 A1 | 8/2005 | Mann et al. |
| 2005/0173245 A1 | 8/2005 | Feldman et al. |
| 2005/0176136 A1 | 8/2005 | Burd et al. |
| 2005/0177036 A1 | 8/2005 | Shults et al. |
| 2005/0181012 A1 | 8/2005 | Saint et al. |
| 2005/0182306 A1 | 8/2005 | Sloan |
| 2005/0182366 A1 | 8/2005 | Vogt et al. |
| 2005/0182451 A1 | 8/2005 | Griffin et al. |
| 2005/0187720 A1 | 8/2005 | Goode, Jr. et al. |
| 2005/0192557 A1 | 9/2005 | Brauker et al. |
| 2005/0195930 A1 | 9/2005 | Spital et al. |
| 2005/0199494 A1 | 9/2005 | Say et al. |
| 2005/0203360 A1 | 9/2005 | Brauker et al. |
| 2005/0203461 A1 | 9/2005 | Flaherty et al. |
| 2005/0214892 A1 | 9/2005 | Kovatchev et al. |
| 2005/0215871 A1 | 9/2005 | Feldman et al. |
| 2005/0215872 A1 | 9/2005 | Berner et al. |
| 2005/0235732 A1 | 10/2005 | Rush |
| 2005/0238503 A1 | 10/2005 | Rush et al. |
| 2005/0238507 A1 | 10/2005 | DiIanni et al. |
| 2005/0239154 A1 | 10/2005 | Feldman et al. |
| 2005/0239518 A1 | 10/2005 | D'Agostino et al. |
| 2005/0245795 A1 | 11/2005 | Goode, Jr. et al. |
| 2005/0245799 A1 | 11/2005 | Brauker et al. |
| 2005/0249506 A1 | 11/2005 | Fuse |
| 2005/0249606 A1 | 11/2005 | Rush |
| 2005/0251083 A1 | 11/2005 | Carr-Brendel et al. |
| 2005/0261660 A1 | 11/2005 | Choi |
| 2005/0267780 A1 | 12/2005 | Ray et al. |
| 2005/0271546 A1 | 12/2005 | Gerber et al. |
| 2005/0271547 A1 | 12/2005 | Gerber et al. |
| 2005/0272640 A1 | 12/2005 | Doyle, III et al. |
| 2005/0272985 A1 | 12/2005 | Kotulla et al. |
| 2005/0277844 A1 | 12/2005 | Strother et al. |
| 2005/0287620 A1 | 12/2005 | Heller et al. |
| 2006/0001538 A1 | 1/2006 | Kraft et al. |
| 2006/0001550 A1 | 1/2006 | Mann et al. |
| 2006/0001551 A1 | 1/2006 | Kraft et al. |
| 2006/0003398 A1 | 1/2006 | Heller et al. |
| 2006/0004271 A1 | 1/2006 | Peyser et al. |
| 2006/0007017 A1 | 1/2006 | Mann et al. |
| 2006/0015020 A1 | 1/2006 | Neale et al. |
| 2006/0015024 A1 | 1/2006 | Brister et al. |
| 2006/0016700 A1 | 1/2006 | Brister et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0025663 A1 | 2/2006 | Talbot et al. |
| 2006/0031094 A1 | 2/2006 | Cohen et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0036187 A1 | 2/2006 | Vos et al. |
| 2006/0040402 A1 | 2/2006 | Brauker et al. |
| 2006/0041229 A1 | 2/2006 | Garibotto et al. |
| 2006/0052679 A1 | 3/2006 | Kotulla et al. |
| 2006/0058602 A1 | 3/2006 | Kwiatkowski et al. |
| 2006/0058627 A1 | 3/2006 | Flaherty et al. |
| 2006/0063218 A1 | 3/2006 | Bartowiak et al. |
| 2006/0074564 A1 | 4/2006 | Bartkowiak et al. |
| 2006/0166629 A1 | 7/2006 | Reggiardo |
| 2006/0173259 A1 | 8/2006 | Flaherty et al. |
| 2006/0173444 A1 | 8/2006 | Choy et al. |
| 2006/0178633 A1 | 8/2006 | Garibotto et al. |
| 2006/0222566 A1 | 10/2006 | Brauker et al. |
| 2006/0224141 A1 | 10/2006 | Rush et al. |
| 2006/0247508 A1 | 11/2006 | Fennell |
| 2006/0253085 A1 | 11/2006 | Geismar et al. |
| 2006/0273759 A1 | 12/2006 | Reggiardo |
| 2006/0282290 A1 | 12/2006 | Flaherty et al. |
| 2007/0016381 A1 | 1/2007 | Kamath et al. |
| 2007/0078323 A1 | 4/2007 | Reggiardo et al. |
| 2007/0106135 A1 | 5/2007 | Sloan |
| 2007/0118405 A1 | 5/2007 | Campbell et al. |
| 2007/0135697 A1 | 6/2007 | Reggiardo |
| 2007/0163880 A1 | 7/2007 | Woo et al. |
| 2007/0173711 A1 | 7/2007 | Shah et al. |
| 2007/0203966 A1 | 8/2007 | Brauker et al. |
| 2007/0219480 A1 | 9/2007 | Kamen et al. |
| 2007/0219597 A1 | 9/2007 | Kamen et al. |
| 2007/0235331 A1 | 10/2007 | Simpson et al. |

| | | |
|---|---|---|
| 2008/0021666 A1 | 1/2008 | Goode, Jr. et al. |
| 2008/0033254 A1 | 2/2008 | Kamath et al. |
| 2008/0045824 A1 | 2/2008 | Tapsak et al. |
| 2008/0064941 A1 | 3/2008 | Funderburk et al. |
| 2008/0071156 A1 | 3/2008 | Brister et al. |
| 2008/0083617 A1 | 4/2008 | Simpson et al. |
| 2008/0086042 A1 | 4/2008 | Brister et al. |
| 2008/0086044 A1 | 4/2008 | Brister et al. |
| 2008/0086273 A1 | 4/2008 | Shults et al. |
| 2008/0103447 A1 | 5/2008 | Reggiardo et al. |
| 2008/0108942 A1 | 5/2008 | Brister et al. |
| 2008/0183061 A1 | 7/2008 | Goode et al. |
| 2008/0183399 A1 | 7/2008 | Goode et al. |
| 2008/0188731 A1 | 8/2008 | Brister et al. |
| 2008/0189051 A1 | 8/2008 | Goode et al. |
| 2008/0194935 A1 | 8/2008 | Brister et al. |
| 2008/0194936 A1 | 8/2008 | Goode et al. |
| 2008/0194937 A1 | 8/2008 | Goode et al. |
| 2008/0194938 A1 | 8/2008 | Brister et al. |
| 2008/0195232 A1 | 8/2008 | Carr-Brendel et al. |
| 2008/0195967 A1 | 8/2008 | Goode et al. |
| 2008/0197024 A1 | 8/2008 | Simpson et al. |
| 2008/0200788 A1 | 8/2008 | Brister et al. |
| 2008/0200789 A1 | 8/2008 | Brister et al. |
| 2008/0200791 A1 | 8/2008 | Simpson et al. |
| 2008/0208025 A1 | 8/2008 | Shults et al. |
| 2008/0214915 A1 | 9/2008 | Brister et al. |
| 2008/0214918 A1 | 9/2008 | Brister et al. |
| 2008/0228051 A1 | 9/2008 | Shults et al. |
| 2008/0228054 A1 | 9/2008 | Shults et al. |
| 2008/0242961 A1 | 10/2008 | Brister et al. |
| 2008/0262469 A1 | 10/2008 | Brister et al. |
| 2008/0275313 A1 | 11/2008 | Brister et al. |
| 2008/0287764 A1 | 11/2008 | Rasdal et al. |
| 2008/0287765 A1 | 11/2008 | Rasdal et al. |
| 2008/0287766 A1 | 11/2008 | Rasdal et al. |
| 2008/0296155 A1 | 12/2008 | Shults et al. |
| 2008/0306368 A1 | 12/2008 | Goode et al. |
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2009/0012379 A1 | 1/2009 | Goode et al. |
| 2009/0018424 A1 | 1/2009 | Kamath et al. |
| 2009/0030294 A1 | 1/2009 | Petisce et al. |
| 2009/0036758 A1 | 2/2009 | Brauker et al. |
| 2009/0036763 A1 | 2/2009 | Brauker et al. |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0045055 A1 | 2/2009 | Rhodes et al. |
| 2009/0062633 A1 | 3/2009 | Brauker et al. |
| 2009/0062635 A1 | 3/2009 | Brauker et al. |
| 2009/0068954 A1 | 3/2009 | Reggiardo et al. |
| 2009/0076356 A1 | 3/2009 | Simpson et al. |
| 2009/0076358 A1 | 3/2009 | Reggiardo et al. |
| 2009/0076360 A1 | 3/2009 | Brister et al. |
| 2009/0076361 A1 | 3/2009 | Kamath et al. |
| 2009/0083003 A1 | 3/2009 | Reggiardo et al. |
| 2009/0099436 A1 | 4/2009 | Brister et al. |
| 2009/0124877 A1 | 5/2009 | Goode, Jr. et al. |
| 2009/0124878 A1 | 5/2009 | Goode et al. |
| 2009/0124879 A1 | 5/2009 | Brister et al. |
| 2009/0124964 A1 | 5/2009 | Leach et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0137886 A1 | 5/2009 | Shariati et al. |
| 2009/0137887 A1 | 5/2009 | Shariati et al. |
| 2009/0143659 A1 | 6/2009 | Li et al. |
| 2009/0143660 A1 | 6/2009 | Brister et al. |
| 2009/0156919 A1 | 6/2009 | Brister et al. |
| 2009/0156924 A1 | 6/2009 | Shariati et al. |
| 2009/0163790 A1 | 6/2009 | Brister et al. |
| 2009/0163791 A1 | 6/2009 | Brister et al. |
| 2009/0178459 A1 | 7/2009 | Li et al. |
| 2009/0182217 A1 | 7/2009 | Li et al. |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Kamath et al. |
| 2009/0192751 A1 | 7/2009 | Kamath et al. |
| 2009/0203981 A1 | 8/2009 | Brauker et al. |
| 2009/0204341 A1 | 8/2009 | Brauker et al. |
| 2009/0216103 A1 | 8/2009 | Brister et al. |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0242399 A1 | 10/2009 | Kamath et al. |
| 2009/0242425 A1 | 10/2009 | Kamath et al. |
| 2009/0247855 A1 | 10/2009 | Boock et al. |
| 2009/0247856 A1 | 10/2009 | Boock et al. |
| 2009/0287073 A1 | 11/2009 | Boock et al. |
| 2009/0287074 A1 | 11/2009 | Shults et al. |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2009/0299276 A1 | 12/2009 | Brauker et al. |
| 2010/0010324 A1 | 1/2010 | Brauker et al. |
| 2010/0010331 A1 | 1/2010 | Brauker et al. |
| 2010/0010332 A1 | 1/2010 | Brauker et al. |
| 2010/0016687 A1 | 1/2010 | Brauker et al. |
| 2010/0016698 A1 | 1/2010 | Rasdal et al. |
| 2010/0022855 A1 | 1/2010 | Brauker et al. |
| 2010/0030038 A1 | 2/2010 | Brauker et al. |
| 2010/0030053 A1 | 2/2010 | Goode, Jr. et al. |
| 2010/0030484 A1 | 2/2010 | Brauker et al. |
| 2010/0030485 A1 | 2/2010 | Brauker et al. |
| 2010/0036215 A1 | 2/2010 | Goode, Jr. et al. |
| 2010/0036216 A1 | 2/2010 | Goode, Jr. et al. |
| 2010/0036222 A1 | 2/2010 | Goode, Jr. et al. |
| 2010/0036223 A1 | 2/2010 | Goode, Jr. et al. |
| 2010/0036225 A1 | 2/2010 | Goode, Jr. et al. |
| 2010/0041971 A1 | 2/2010 | Goode, Jr. et al. |
| 2010/0045465 A1 | 2/2010 | Brauker et al. |
| 2010/0049024 A1 | 2/2010 | Saint et al. |
| 2010/0063373 A1 | 3/2010 | Kamath et al. |
| 2010/0076283 A1 | 3/2010 | Simpson et al. |
| 2010/0081908 A1 | 4/2010 | Dobbles et al. |
| 2010/0081910 A1 | 4/2010 | Brister et al. |
| 2010/0087724 A1 | 4/2010 | Brauker et al. |
| 2010/0096259 A1 | 4/2010 | Zhang et al. |
| 2010/0099970 A1 | 4/2010 | Shults et al. |
| 2010/0099971 A1 | 4/2010 | Shults et al. |
| 2010/0119693 A1 | 5/2010 | Tapsak et al. |
| 2010/0121169 A1 | 5/2010 | Petisce et al. |

FOREIGN PATENT DOCUMENTS

| | | |
|---|---|---|
| EP | 0518524 | 12/1992 |
| EP | 0878707 | 11/1998 |
| EP | 0543916 | 7/2001 |
| EP | 1130638 | 9/2001 |
| EP | 1755443 | 11/2005 |
| EP | 1783536 | 5/2007 |
| JP | 2001-177423 | 6/2001 |
| JP | 2001-056673 | 11/2001 |
| WO | WO-96/14026 | 5/1996 |
| WO | WO-99/22236 | 5/1999 |
| WO | WO-01/52727 | 7/2001 |
| WO | WO-01/71186 | 9/2001 |
| WO | WO-02/39086 | 5/2002 |
| WO | WO-02/084860 | 10/2002 |
| WO | WO-02/100263 | 12/2002 |
| WO | WO-02/100469 | 12/2002 |
| WO | WO-03/006091 | 1/2003 |
| WO | WO-2004/028337 | 4/2004 |
| WO | WO-2004/032994 | 4/2004 |
| WO | WO-2004/061420 | 7/2004 |
| WO | WO-2005/089103 | 9/2005 |
| WO | WO-2005/101994 | 11/2005 |
| WO | WO-2006/003919 | 1/2006 |
| WO | WO-2006/079114 | 7/2006 |
| WO | WO-2006/086701 | 8/2006 |

| | | |
|---|---|---|
| WO | WO-2006/102412 | 9/2006 |
| WO | WO-2006/110913 | 10/2006 |
| WO | WO-2006/113408 | 10/2006 |
| WO | WO-2006/113521 | 10/2006 |
| WO | WO-2006/118947 | 11/2006 |
| WO | WO-2006/132884 | 12/2006 |
| WO | WO-2007/041072 | 4/2007 |
| WO | WO-2008/055037 | 5/2008 |

OTHER PUBLICATIONS

Barbosa, R. M., et al., "Electrochemical Studies of Zinc in Zinc-Insulin Solution", *Journal of the Royal Society of Chemistry, Analyst*, vol. 121, No. 12, 1996, pp. 1789-1793.

"An Electrochemical Slow Flow Meter", http://gore.ocean.washington.edu/research/slow_flow_meter.html, 2005, 3 pages.

Bard, A. J., et al., "Methods Involving Forced Convection—Hydrodynamic Methods", *Electrochemical Methods—Fundamentals and Applications*, 2001, pp. 331-367.

Kissinger, P. T., "Introduction to Analog Instrumentation", *Laboratory Techniques in Electroanalytical Chemistry, Second Edition, Revised and Expanded*, 1996, pp. 165-194.

Ursino, M, et al., "A Mathematical Model of Cerebral Blood Flow Chemical Regulation—Part I: Diffusion Processes", *IEEE Transactions on Biomedical Engineering*, vol. 36, No. 2, 1989, pp. 183-191.

International Search Report and Written Opinion of the International Searching Authority for PCT Patent Application Serial No. PCT/US2007/061072 filed Jan. 25, 2007.

European Patent Application No. 07762825.3, Extended European Search Report mailed May 20, 2010.

\* cited by examiner

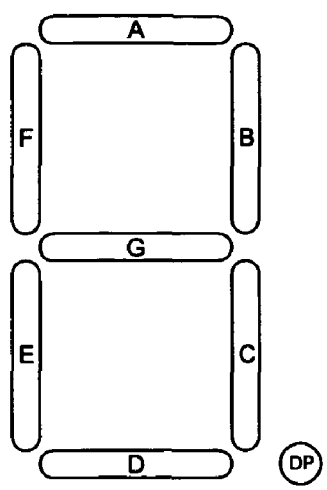
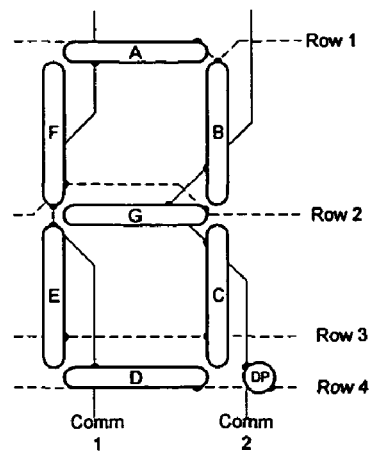
Figure 2A
FIGURE 3A  FIGURE 3B
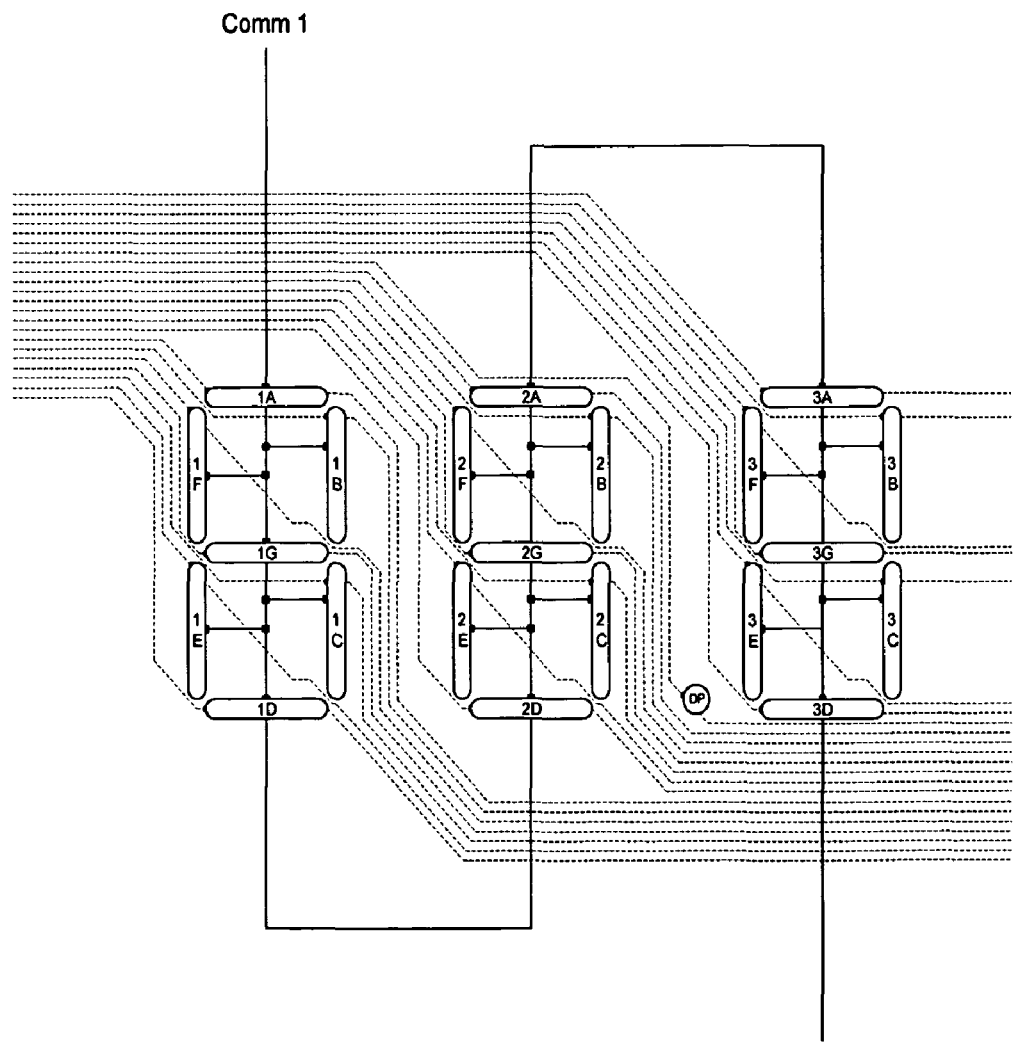
FIGURE 4

METHOD AND SYSTEM FOR PROVIDING A FAULT TOLERANT DISPLAY UNIT IN AN ELECTRONIC DEVICE

BACKGROUND

In a conventional seven segment display such as those used on LCDs (Liquid Crystal Displays), the display wiring is routed without consideration for fault tolerance, and the icon (or pixel) selection matrix is typically generated to match the display. Such configuration allows for erroneous results to be displayed and could potentially result in patient mistreatment, for example, in the case where the seven segment display configurations are used in medical devices such as, but not limited to, glucose meters.

By way of an example, a glucose reading from a blood glucose meter used by diabetic patients that shows a value of 150 when in fact the actual measured value from the test strip using the glucose meter is 450 will inform the patient that they are in a good (clinically acceptable) range when in fact, the patient's condition requires immediate medical attention, for example. In addition, a failure of a decimal point in the displayed value may also erroneously inform the patient to take corrective actions that are either inaccurate (and thus potentially harmful), or to provide the patient with false positive values (those values are erroneous readings but are good values in the context of health treatment).

While some erroneous displayed values may be acceptable and thus not medically significant (such as, for example a glucose reading of 163 mg/dL which is erroneously displayed as 153 mg/dL), those other erroneous displayed values may potentially guide the patient to take corrective actions that are in fact therapeutically inappropriate (or alternatively, providing a false sense of accuracy, to guide the patient to take no action at all, when in fact, corrective medical action is necessary, as described above).

In view of the foregoing, it would be desirable to have an approach to provide fault tolerance in the display unit of an electronic device including medical devices such that failure modes of the electronic device display unit will show output values to the patient or the user of the electronic device that are either nonsensical, or clinically insignificant. In this manner, the failed display unit of the electronic device does not erroneously impact the patient decision based on the output display of the electronic device. Moreover, when a nonsensical value is displayed, the user of the electronic device such as a medical device will be aware that the device is malfunctioning, and will likely not continue its use.

SUMMARY OF THE INVENTION

In view of the foregoing, in accordance with the various embodiments of the present invention, there is provided a method and system for fault tolerant configurations of a seven segment display of an electronic device including medical devices such as the LCD display of a glucose meter. For example, in certain embodiments if an LCD failure occurs, the result displayed will not be a number, or alternatively, the erroneous number displayed are in the A or B region of the Clarke Error Grid (that is, in the acceptable range of values in the case of measured glucose values) or analogous range of an other analysis protocol, e.g., Parks Error Grid, Continuous Glucose Error Grid, MARD analysis, and the like. Therefore, fault tolerance minimizes the chance of an incorrect number being displayed and reduces the effect of a potential error on patient treatment.

More specifically, in accordance with the various embodiments of the present invention, there is provided a fault tolerant display unit which may be configured to mitigate the effects of a display failure. More specifically, in one embodiment, if a display failure occurs (by, for example, a single pixel or multiple pixel failures), the displayed results may be configured to display an invalid number. Alternatively, in the case of glucose meters, the display failure may be mitigated by displaying, in one embodiment, measured glucose values that are within the A or B region of the Clarke Error Grid or the like, and thus, the error is not clinically significant to the patient using the glucose meter.

In this manner, in one embodiment, the probability of an incorrect value being displayed can be minimized, and the effect of a potential error on the patient treatment (based on incorrect value) may be reduced if an incorrect number is displayed.

These and other objects, features and advantages of the present invention will become more fully apparent from the following detailed description of the embodiments, the appended claims and the accompanying drawings.

BRIEF DESCRIPTION OF THE DRAWINGS

FIG. 3A illustrates a single digit segment with icons in an LCD display unit including a decimal point segment;

FIG. 3B illustrates the single digit segment with icons in the LCD display unit including the decimal point segment of FIG. 3A with multiple common line connectors (pads) and row connections;

FIG. 4 illustrates a three digit segment of an LCD display unit with typical connections for a typical electronic device;

DETAILED DESCRIPTION

Figure 1:
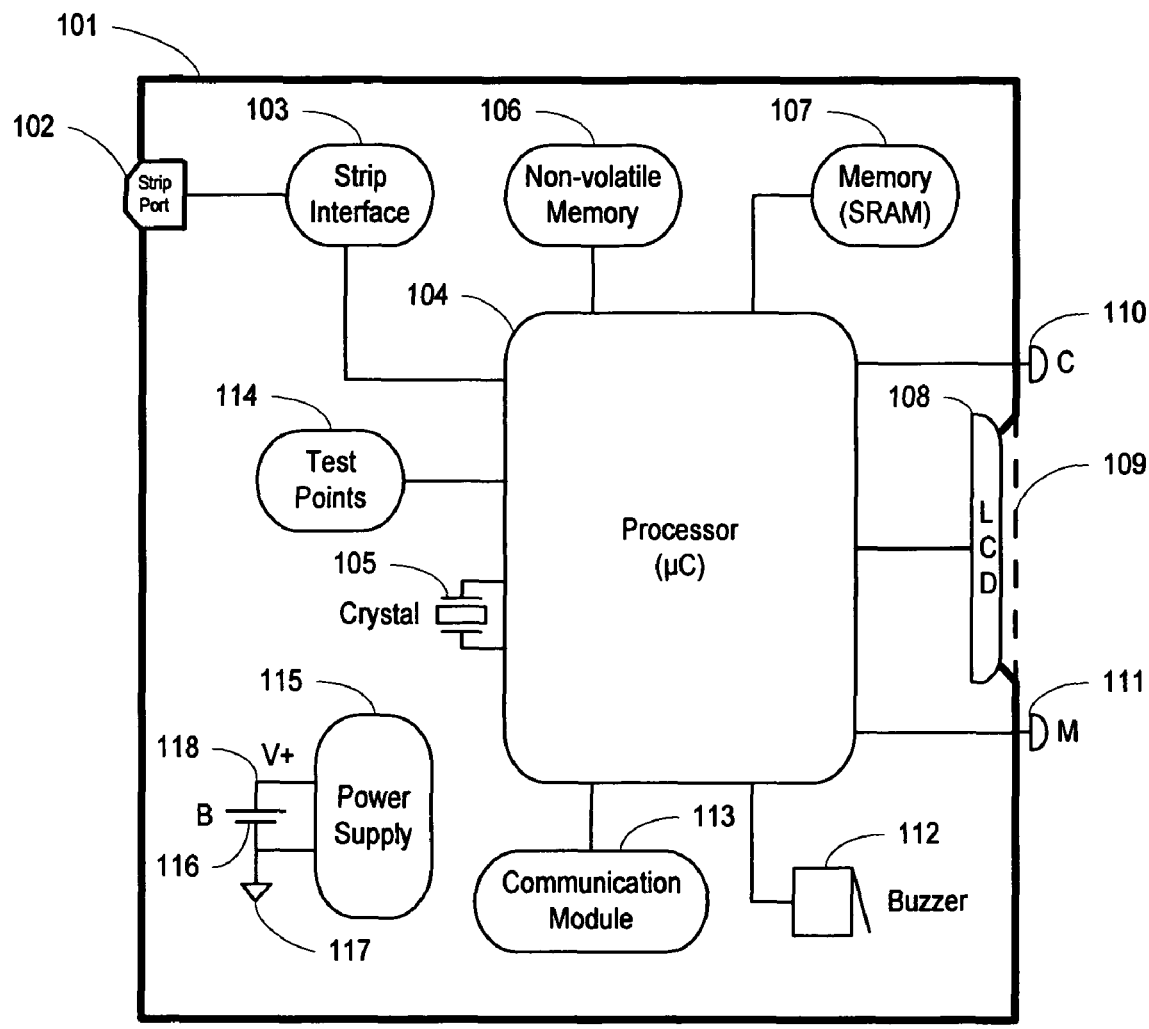
FIG. 1 is a block diagram of a fault tolerant display unit for an electronic device in accordance with one embodiment of the present invention.

FIG. 1 is a block diagram of a fault tolerant display unit for an electronic device in accordance with one embodiment of the present invention. Referring to the figure, the fault tolerant display unit 100 of a blood glucose meter 101 in one embodiment includes a strip port 102 that is configured to receive a glucose test strip. The strip port 102 is coupled to a strip interface 103 which is configured to process the analog signals received from the strip port 102 and converts the signals to corresponding digital values. Also, a controller unit such as a microprocessor 104 is operatively coupled to the strip interface 103 and is configured to process the digital data received from the strip interface 103.

A crystal 105 may be provided and operatively coupled to the microprocessor 104, and configured to set timing for the microprocessor 104 such that the information or data received from the strip interface 103 has a predetermined and known timing and an accurate glucose value may be determined. Additionally, a non-volatile memory 106 may be operatively coupled to the microprocessor 104 and configured for storing program processes such as algorithms, setup and/or calibration parameters as well as glucose readings received from the strip port 102. A temporary storage device such as SRAM 107 or the like may be provided and operatively coupled to the microprocessor 104, for temporary data storage and program execution.

Also shown is a display unit 108 which may include a liquid crystal display (LCD) for output, displaying data and information. An LCD lens 109 is also provided and includes the clear section of the display unit housing that permits the LCD display unit 108 to be viewed. Input devices 110 and 111 are also provided and operatively coupled to the microprocessor 104, and configured to allow the user of the glucose meter 101 to input information and/or control the glucose meter 101 by operating as the user interface providing a user menu navigation. A control button 110 and mode button 111 may be provided to allow the user to toggle between various operational modes for the glucose meter 101 including, for example, calibration, data, recall, storage, and the like.

Referring still to FIG. 1, an audio output unit such as a buzzer 112 may be provided to provide audible alert and/or alarms, indicating a condition of the functional properties of the glucose meter 101 or, provide an audible indication of a data received by the glucose meter 101, for example. A communication module 113 is operatively coupled to the microprocessor 104, and configured to download glucose readings from a data storage log stored in the non-volatile memory 106. Moreover, a set of test points 114 may be made available within the blood glucose meter 101 housing for manufacturing processes. Additionally, a power supply 115 is provided to provide power to the blood glucose meter 101, and may include a battery 116 for example, such as, for example CR30232 Lithium Ion Coin Cell battery or the like configured as the primary power source for the power supply 115. In further detail, the battery 116 may be connected to the blood glucose meter 101 ground terminal 117, and the battery 116 may be configured to provide power to the power supply 115 positive voltage input terminal (V+) 118.

Additional features such as an LCD backlight or test light to illuminate the strip port may be provided to the blood glucose meter 101. The controller unit 104 may be a microcontroller (μC) such as the MSP430FG439 that may incorporate the strip interface 103, non-volatile memory 106, memory (SRAM) 107, controller for the LCD 108, and interface for the communications module 113. Moreover, the controller unit 104 may be configured to control the operations of the various components of the blood glucose meter 101 as shown in FIG. 1, under the control of, for example, the patient using the blood glucose meter 101 providing commands or instructions using the input units 110 or 111. In one embodiment, the blood glucose meter 101 may be configured to display glucose values in the range of about 20 mg/dL to about 500 mg/dL (or about 600 mg/dL for hospital use), or about 1.1 mmol/L to about 27.8 mmol/L (or about 33.3 mmol/L for hospital use).

Figure 2A:
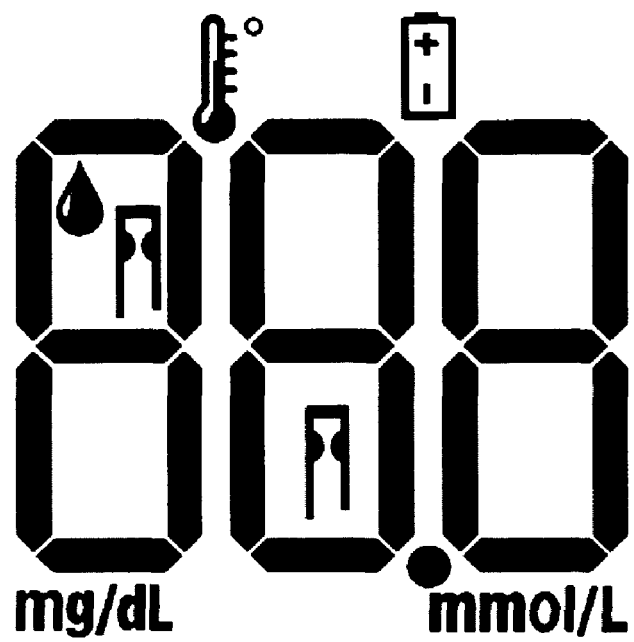
FIGS. 2A-2B illustrate exemplary segmented display units including icons of a blood glucose meter device.
Figure 2B:
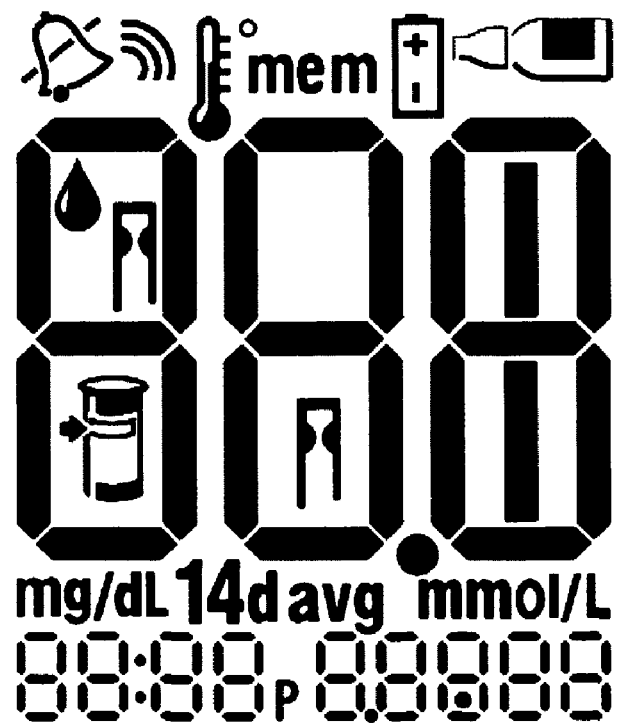

FIGS. 2A-2B illustrate exemplary segmented display units including icons of a blood glucose meter device. Referring to FIG. 2A, for an electronic device, e.g., a medical device such as a blood glucose meter as shown in FIG. 1, the minimum LCD requirement includes the glucose value display (three 7-segment digits), a "mmol/L" icon (with the decimal point active), a "mg/dL" icon (with the decimal point inactive), a temperature out-of-range indicator, a low-battery indicator, and an "apply blood to test strip" set of symbols as respectively shown by the corresponding icons in FIG. 2A. Referring to FIG. 2B, additional features and or configurations of a blood glucose meter LCD display unit may include the ability to set the date and time information, and further, to display stored memory log entries (prior glucose readings) with associated date and time. Additional features may include the ability to set a strip calibration code, to display a multiple day (e.g., 14-day) average glucose reading based on log entries, set configuration options such as alarm audible or silent, and identify a glucose log entry as a control reading.

FIG. 3A illustrates a labeled or numbered single digit segment with icons in an LCD display unit including a decimal point segment, and FIG. 3B illustrates the single digit segment with icons in the LCD display unit including the decimal point segment of FIG. 3A with control signals in the form of multiple common line connectors and row connections, where each common line or row connections is known as a "pad". Referring to FIG. 3A, each of the seven segments A, B, C, D, E, F, and G are separately provided and none are electrically connected to any of the other segments (and where each may be individually controlled).

In FIG. 3B, it can be seen that several segments are connected by one of the three row connectors and/or one of the two common (column) connectors. For example, row 1 connector as shown in FIG. 3B is connected to segments A and B, the row 2 connector is connected to segments F and G, and the row 3 connector is connected to segments C and E, while row 4 is connected to segment D and the decimal point DP. Moreover, common 1 connector as shown in FIG. 3B are connected to segments A, D, E, and F, while common 2 connector is connected to segments B, C, G and the decimal point DP segment. In this manner, in FIG. 3B, if the connection (pad) for comm 1 fails, then segments A, D, E and F will not activate and, for example, a "7" will be displayed as a "1".

FIG. 4 illustrates a three digit segment of an LCD display unit with typical connections for an electronic device. Referring to FIG. 4, there is provided a mapping of which segments of the display are used to display each number. More specifically, it can be seen that the row and column connections only cross other rows or columns where pixels (segments) are formed. The row signals (lines) are located on one plane of the display and the common lines are located on another such that a segment (or pixel) is formed inside the LCD at the crossing point.

There are several different types of common LCD failures. A connector failure occurs when the connection between the printed circuit board (PCB) and LCD connector fails to make contact. Some examples include, but is not limited to, heat-seal failures, zebra strip failures and pad failures. A driver failure occurs when the LCD driver fails to operate properly. Some examples include ESD and other types of LCD driver failures. Finally, a connector short failure occurs when foreign material is introduced onto the connector causing two or more signals or pads to short together. When this type of failure occurs, most errors that result in a number will tend towards an eight ("8"). Since the blood glucose meter 101 does not have an eight in the first digit of its display, this type of error, though it must be checked for each individual design, tends to result in A or B region errors on the Clarke Error Grid even if they occur in the second digit, or numbers that are beyond the glucose meter range, or nonsensical numbers.

Failure modes for the blood glucose meter 101 includes (1) failure of a row or common, (2) a first digit error, (3) missing decimal point or first digit, or (4) other digit errors. When a row or common line fails, all segments connected to that row or common line fail and is commonly caused by connector failure. For example, referring for example to FIG. 4, if common 1 connector fails, all segments in the display fails to function as all seven segments of all three digits are connected to the common 1 connector.

When a first digit error occurs due to a poor connection, for example, a first digit "4" or "3" becomes a "1", such that, for example, a "4xx" value is displayed as "1xx", and "3xx" is displayed as "1xx", respectively. When there is a missing decimal point or a first digit, a failure of this type generally results in a critical error and is also commonly found with a connector failure. This error results in the entire first digit not being displayed or the decimal point missing, and may result in an error as great as an entire order of magnitude. An error on this scale may result in patient mistreatment, and tends to fall in the D or E regions of the Clarke Error Grid.

When digit errors occur, a given digit of a seven segment display is erroneously displayed because of a segment failure within the seven segment display for the particular digit. Examples of digit errors are further illustrated by the Table A shown below which illustrates the original display (or the proper or accurate display) in the first column, and the actual display with the digit error in the second column, and the missing segment causing the digit error in the third column. For example, with reference to FIG. 3A and Table A below, when the seven segment digit is missing the E segment, an original display of the value "6" which comprises segments A, C, D, E, F, and G, will actually be displayed as a "5" (comprised of segments A, C, D, F, and G). For a three digit display, the first digit is the most critical (as it is the most significant value), the second digit can result in A or B region errors on the Clarke Error Grid and the third digit can only result in the A region errors making it the least critical digit.

TABLE A

| Original Display | Number Displayed in Error | Segments Missing |
|---|---|---|
| 6 | 5 | E |
| 7 | 1 | A |
| 8 | 0 | G |
| 3 | 7 | D, G |
| 4 | 1 | F, G |
| 8 | 2 | F, C |
| 8 | 5 | B, E |
| 8 | 9 | D, E |
| 9 | 7 | F, G |
| 3 | 1 | A, D, G |
| 9 | 1 | A, F, G |
| 8 | 7 | D, E, F, G |

In the manner shown above, it can be seen that even with a single segment failure, a significant or critical error may be displayed if the failed segment is associated with the most significant digit in, for example, a three digit display unit. That is, referring to the Table A above, a failed segment G will result in the number 8" to be displayed as "0", which error may be significant in the context of values or measurements of a patient parameter upon which medical treatment is based (note that an value of 180 displayed as a 100 is in the B region of the Clarke Error Grid in the case of glucose measurements).

Figure 5:
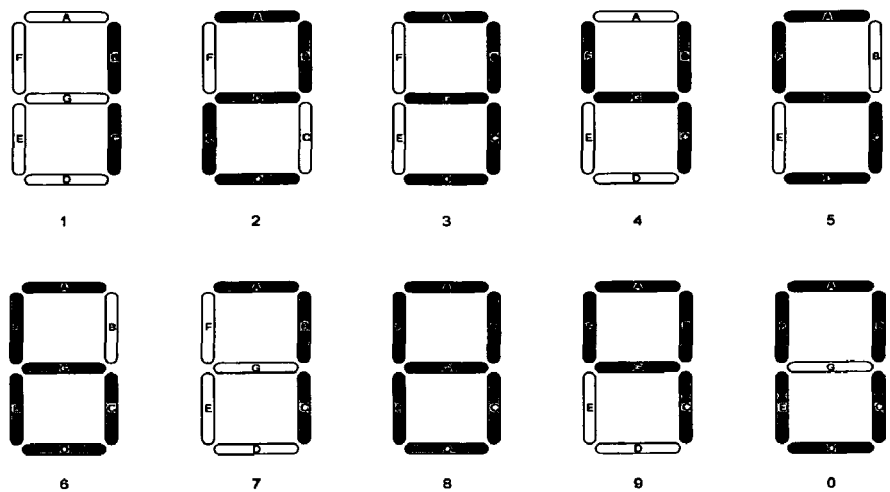
FIG. 5 illustrates the digits 0 to 9 of a seven-segment display used for determining fault tolerance in an LCD display unit of an electronic device in accordance with one embodiment of the present invention.

FIG. 5 illustrates the digits "0" to "9" and is the basis for the method of checking for fault tolerance in an LCD display unit of an electronic device in accordance with one embodiment of the present invention. Referring to FIGS. 1 and 5, for a seven-segment digit display unit as described, it is possible to determine or check for fault tolerance based on the connection of the various segments on each row or column connector. That is, in one embodiment, for each row or column connector that connects a predetermined set of segments together, a layout similar to that shown in FIG. 5 may be generated which illustrates, for example, a row connector based on a single pad failure in which segments A and F are not functioning.

Referring again to FIG. 5, with the segments A and F in failure mode, the only number or value whose displayed accuracy is maintained is value "1", while the value for the original number "7" is erroneously shown as a "1". All other remaining values are provided as nonsensical number. For example, the original number "2" is now displayed with the top A segment disabled which has no representative value. In this manner, it is possible to determine the impact of row or common connector failures on a seven segment display.

Figure 6A:
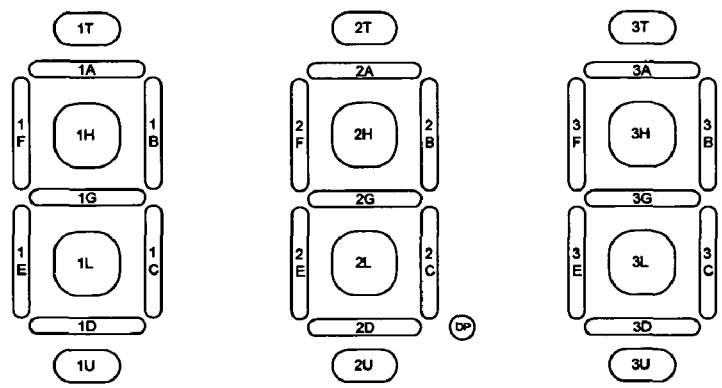
FIG. 6A illustrates a three digit segment layout with icons for an electronic device LCD display unit.
Figure 6B:
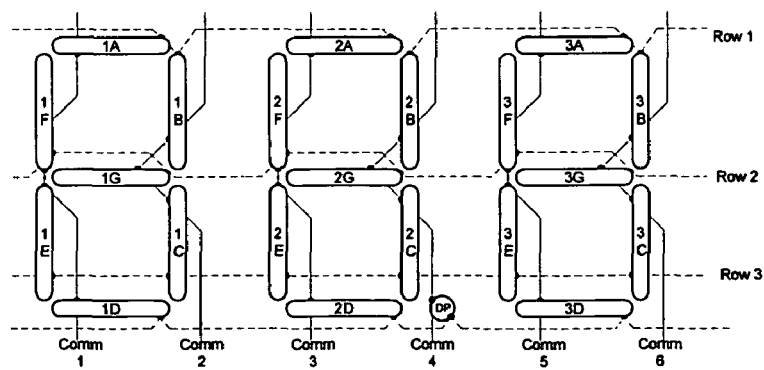
FIG. 6B illustrates the three digit segment layout of FIG. 6A with multiple row and column connections.

FIG. 6A illustrates a three digit segment layout with icons for an electronic device LCD display unit, and FIG. 6B illustrates the three digit segment layout of FIG. 6A with multiple row and column connectors. More specifically, as shown in FIG. 6B, each of the three row connectors (row 1, row 2 and row 3) and each of the six common connectors (comm 1, comm 2, comm 3, comm 4, comm 5, and comm 6), are respectively connected to a corresponding segment(s) in one or more of the three 7-digit display. For example, it can be seen from FIG. 6B that row 1 connector or pad is connected to segments 1A and 1B of the most significant digit, segments 2A and 2B of the less significant digit, and to segments 3A and 3B of the least significant digit (to the right of the decimal point DP).

A common failure in a seven-segment LCD display unit is having a pad or connector loose contact, resulting in a loss of the respective segment(s). This failure generally occurs near the outer edges of the LCD connector for heat seal connectors. To reduce the impact of this type of failure, in one embodiment, with reference to FIG. 6B, the critical segments of the display (for example, segments whose failures have substantial impact upon the displayed readout) may be located near the middle of the connector. When this type of failure occurs, often there are two adjacent pads that fail simultaneously. In order to avoid losing two critical segments at the same time, a pad or connector that is not as critical, such as that connected to a non critical icon, may be positioned between the two critical segments.

Moreover, this approach in one embodiment may be applied to the display unit configuration as shown in FIG. 4 that includes a single common connector (comm1) with multiple pad connectors. Furthermore, the decimal point for such displays as shown in FIG. 4 may be controlled by a pad such that it is between the pads controlling segments C and D of a relevant digit. This approach in one embodiment may not prevent all errors from occurring, but will mitigate the effect and frequency of these errors as either segments C or D are used in each number displayed.

Figure 7:
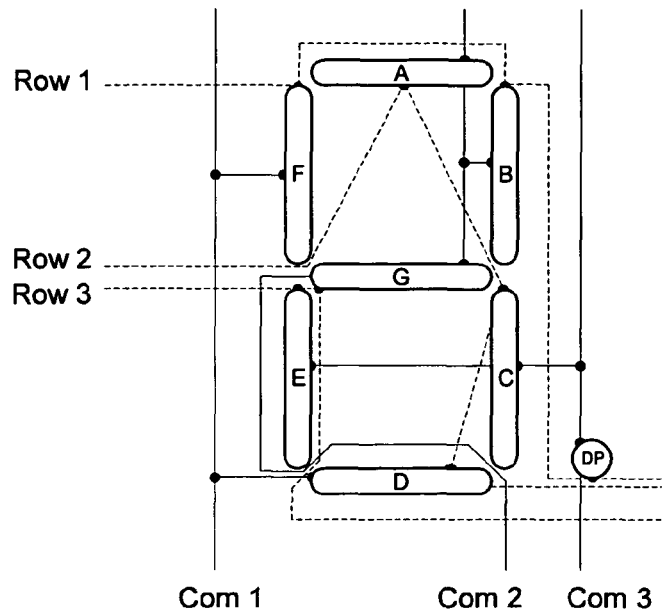
FIG. 7 illustrates a segmented display configuration for 3×3 mapping in a fault tolerant display system in accordance with one embodiment of the present invention.

FIG. 7 illustrates a segmented display configuration for 3×3 mapping in a fault tolerant display system in accordance with one embodiment of the present invention. Referring to FIG. 7, the seven segments and the decimal point DP are each correspondingly connected to a plurality of the row or common pad connectors (row 1, row 2, row 3, and comm 1, comm 2, and comm 3), and arranged as shown in Table B below.

TABLE B

|       | Comm 1 | Comm 2 | Comm 3 |
|-------|--------|--------|--------|
| Row 1 | F      | B      | DP     |
| Row 2 | D      | A      | C      |
| Row 3 | **     | G      | E      |

The row 3/comm 1 location indicated with "**" may be used for another icon or other symbols on the display but which is not needed for the primary display segments.

In this manner, it can be seen that the possibility of an erroneous number or value displayed is substantially minimized. More specifically, for example as shown in the embodiment of FIG. 7, when one of the pad connectors (row 1, row 2, row 3, and comm 1, comm 2, and comm 3) fails, then the resulting display will not be a number, but rather, a nonsensical display output. Moreover, the configuration shown in FIG. 7 in one embodiment provides for the decimal point DP to be missing (when the corresponding pad fails) concurrent with a substantially noticeable error in the output value of one of the digits.

For example, if row 2 connector fails, then segments A, C and D fail, resulting in a display of nonsensical number. Moreover, if comm 3 connector fails, then the decimal point DP fails in addition to segments C and E, again, rendering the output display to be nonsensical, and with the disabled decimal point DP. In this manner, in one embodiment of the present invention, a substantially fault tolerant seven segment LCD display configuration is provided which substantially minimizes the possibility of erroneously displaying a value to the patient and which may be the basis of inaccurate and/or inappropriate patient treatment.

Figure 8:
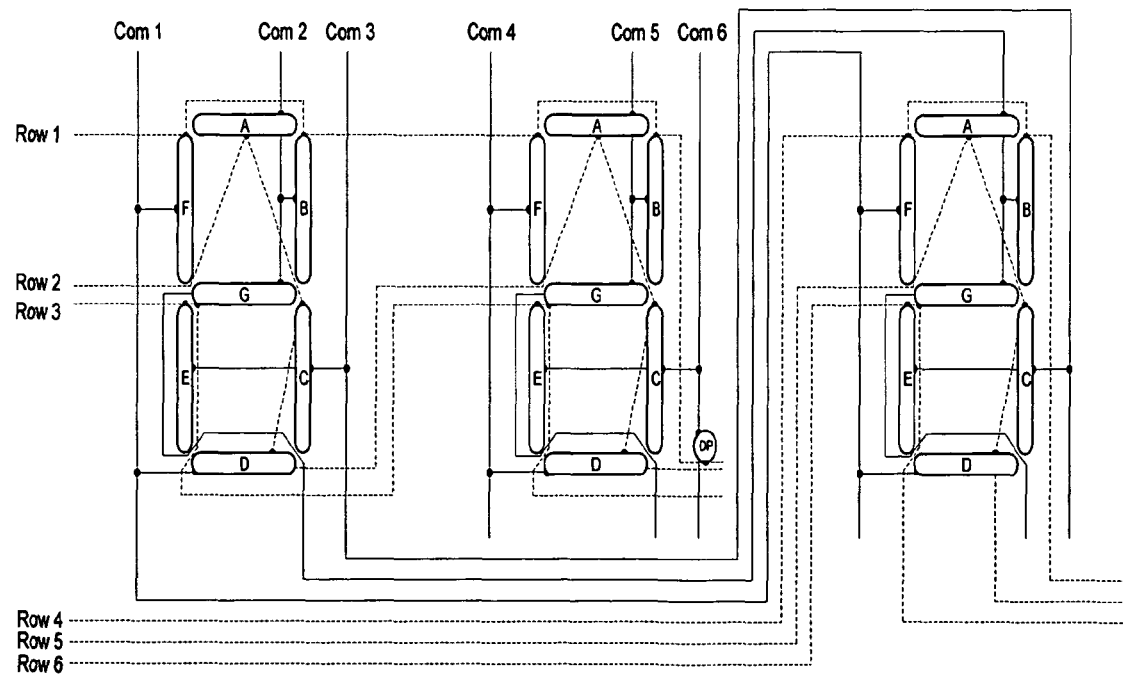
FIG. 8 illustrates a segmented display configuration for 6×6 mapping in a fault tolerant display system in accordance with another embodiment of the present invention.

FIG. 8 illustrates a segmented display configuration for 6×6 mapping in a fault tolerant display system in accordance with another embodiment of the present invention. Referring to FIG. 8, it can be seen that the output display for the 6×6 mapping configuration provides a three digit seven-segment display suitable for a blood glucose meter 101 (FIG. 1) for example, for displaying a range of measured glucose values. More specifically, compared with the embodiment shown in FIG. 7 for a single digit 3×3 mapping of the three row connectors and three common connectors, in the embodiment shown in FIG. 8, there are provided six row connectors (row 1, row 2, row 3, row 4, row 5, and row 6) and six common connectors (comm 1, comm 2, comm 3, comm 4, comm 5, and comm 6) using similar mapping configuration as the single digit configuration of FIG. 7. This configuration provides additional or further fault tolerance against a missing first digit as compared to three 3×3 mapping in sequence.

Figures 9, 10:
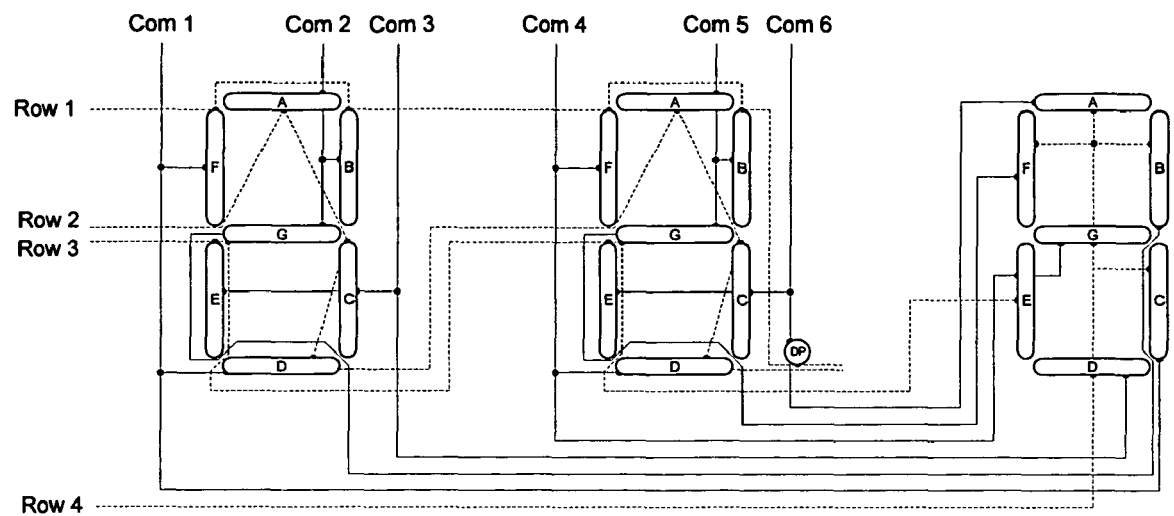
FIG. 9 illustrates a segmented display configuration for 6×4 mapping in a fault tolerant display system in accordance with still another embodiment of the present invention.
FIG. 10 is a tabular illustration of the fault tolerant display for LCD display unit in an electronic device with varying levels of fault tolerance.

FIG. 9 illustrates a segmented display configuration for 6×4 mapping in a fault tolerant display system in accordance with still another embodiment of the present invention. Referring to FIG. 9, provided with four row connectors (row 1, row 2, row 3, and row 4) and six common pads or connectors (comm 1, comm 2, comm 3, comm 4, comm 5, and comm 6), the layout shown in Table C may be used.

TABLE C

|        | Row 4 | Row 3 | Row 2 | Row 1 |
|--------|-------|-------|-------|-------|
| Comm 1 | 3C    | **    | 1D    | 1F    |
| Comm 2 | 3B    | 1G    | 1A    | 1B    |
| Comm 3 | 3D    | 1E    | 1C    | *     |
| Comm 4 | 3G    | 3E    | 2D    | 2F    |
| Comm 5 | 3F    | 2G    | 2A    | 2B    |
| Comm 6 | 3A    | 2E    | 2C    | DP    |

The location indicated with a "*" may be used for a second decimal point (DP) if needed or alternatively, for an icon displayed on the display unit, and the location indicated with a "**" may be used for icons or other symbols on the display but is not needed for the segments.

In one embodiment, the layout shown in FIG. 9 is configured to prevent the first and second digits, including the decimal point, from resulting in a numerical error. The third digit, however, may result in a missing digit or a numerical error. In glucose meters, the errors that result from the third digit will be are sufficiently insignificant (clinically) that they are contained in the A or B region of the Clarke Error Grid, and thus erroneous reading or display will likely not result in substantial misdiagnosis or significant improper treatment of the patient.

FIG. 10 is a tabular illustration of the fault tolerant display for LCD display unit in an electronic device with varying levels of fault tolerance for illustrating the various embodiments of the present invention described herein. For example, a correct reading of a glucose meter at 140 shown by the first entry in the first column in Table C, will result in a bad reading if the most significant digit "1" is missing. Accordingly, in one embodiment, the display unit may be configured such that the bad reading of "40" is instead configured to be output as a good reading as shown in the corresponding row of Table C in the third column. Indeed, the good reading is displayed as a nonsensical value which is not likely to mislead the patient that the 10 measured glucose level is 40 rather than 140 which is the actual accurate value.

In yet another embodiment of the present invention, there is provided a fault tolerant three digit LCD display unit which does not display any cross point pixels (pixels that are always displayed caused by a row connector and a common connector crossing). In this case, a 4×12 mapping may be used in accordance with the layout 15 shown in Table D below which includes twelve row connectors and four common connectors.

TABLE D

|        | Comm 1 | Comm 2 | Comm 3 | Comm 4 |
|--------|--------|--------|--------|--------|
| Row 1  | —      | —      | —      | 1D     |
| Row 2  | —      | —      | 1E     | 1C     |
| Row 3  | 1A     | 1F     | —      | —      |
| Row 4  | —      | 1B     | 1G     | —      |
| Row 5  | —      | —      | 2E     | 2C     |
| Row 6  | 2A     | 2F     | —      | —      |
| Row 7  | —      | 2B     | 2G     | DP     |
| Row 8  | 3A     | 3F     | —      | —      |
| Row 9  | —      | 3B     | 3G     | —      |
| Row 10 | —      | —      | 3E     | 3C     |
| Row 11 | —      | —      | —      | 3D     |
| Row 12 | —      | —      | —      | 2D     |

In this manner, inadvertent display errors may be mitigated while also minimizing the number of cross point pixels on an LCD. The third digit for this method can also be located in other locations in the truth table without sacrificing fault tolerance as it is not a critical digit. The open spaces in Table E shown with the "-" may be used for icons or other symbols, provided that they do not create cross points between the rows and commons (columns). This approach in one embodiment eliminates critical errors, such as missing decimal point and missing first digit, but may not eliminate all errors. However, the errors that occur will fall into either the A or B region of the Clarke Error Grid, that is, within the acceptable tolerance range, and thus prove to be clinically acceptable.

In this manner, in accordance with the various embodiments of the present invention, there is provided a method and system for fault tolerant configuration of a seven segment display of an electronic device including medical devices such as the LCD display of a glucose meter. That is, if an LCD failure occurs, the result displayed will not be a number, or alternatively, the erroneous number displayed are in the A or B region of the Clarke Error Grid (that is, in the acceptable/tolerance range of values in the case of measured glucose values). Therefore, the fault tolerance approach in accordance with the present invention minimizes the chance of an incorrect number being displayed and reduces the effect of a potential error on patient treatment.

In accordance with the various embodiments of the present invention, there is provided a fault tolerant display unit which may be configured to mitigate the effects of display failure. More specifically, in one embodiment, if a display failure occurs (by, for example, a single pixel or multiple pixels failures and/or pad or connector failures), the displayed results may be configured to display an invalid number. Alternatively, in the case of glucose meters, the display failure may be mitigated by displaying, in one embodiment, measured glucose values that are within the A or B region of the Clarke Error Grid.

In this manner, in one embodiment, the probability of an incorrect value being displayed can be minimized, and the effect of a potential error on the patient treatment (based on incorrect value) may be reduced if an incorrect number is displayed.

Indeed, an apparatus including a fault tolerant display unit for an electronic device in one embodiment of the present invention includes a display unit, a controller unit operatively coupled to the display unit, the controller unit configured to control the display unit to display information, where when a failure mode of the display unit occurs, the display unit is configured to display modified information, where the modified information is different from the information for display under the control of the controller unit.

The display unit in one embodiment may include a seven segment Liquid Crystal Display (LCD) unit with one or more digits.

Additionally, the display unit may be configured to display one or more health related values, where the one or more health related values may include one or more of a measured glucose value, a cholesterol level, and a blood alcohol level.

The failure mode of the display unit in one embodiment includes one or more of a connector failure, a display unit driver failure, or a connector short.

Moreover, one of an RF receiver unit, wherein the display unit may be coupled to a housing of the RF receiver unit.

In an another embodiment, an infusion device may also be provided, where the display unit may be coupled to a housing of the infusion device. The infusion device may include an external insulin pump, an implantable insulin pump, or an on-body patch pump.

Moreover, in a further embodiment, a glucose meter may be provided, where the display unit is coupled to a housing of the glucose meter.

The displayed modified information associated with the detected failure mode in one embodiment is non-informative.

A method of providing display fault tolerance in an electronic device in another embodiment includes the steps of receiving one or more commands to display information on a display unit, detecting a failure mode associated with the display unit, and displaying modified information on the display unit associated with the detected failure mode.

In one embodiment, the step of displaying may include the step of disabling a predetermined segment of the information for display such that the displayed information is a subset of the information for display, and further, where the subset of the information for display may be non-informative.

A display unit of an electronic device in yet another embodiment of the present invention includes a display portion, and a controller coupled to the display portion, the display portion configured to display a predetermined information based on one or more commands received from the controller, where, when a failure mode is detected in the display portion, the one or more commands received from the controller to display the predetermined information does not change.

Various other modifications and alterations in the structure and method of operation of this invention will be apparent to those skilled in the art without departing from the scope and spirit of the invention. Although the invention has been described in connection with specific preferred embodiments, it should be understood that the invention as claimed should not be unduly limited to such specific embodiments. It is intended that the following claims define the scope of the present invention and that structures and methods within the scope of these claims and their equivalents be covered thereby.

What is claimed is:

1. A method of providing display fault tolerance in an electronic device, comprising:

receiving one or more commands to display an information on a display unit, the display unit comprising a first display portion including a first plurality of display segments and a first plurality of connectors, a second display portion including a second plurality of display segments and a second plurality of connectors, and a third display portion including a third plurality of display segments and a third plurality of connectors, wherein each connector is connected to a different combination of two or more display segments in one or more of the first display portion, the second display portion, and the third display portion;

detecting a failure mode of the display unit, the failure mode resulting from failure of at least one connector;

determining if the failure is related to one or more of the first display portion, the second display portion, and the third display portion; and displaying a modified information on the display unit indicating the detected failure mode of the display unit if it is determined that the failure is related to at least one of the first display portion and the second display portion, the modified information represented by a first predetermined number of display segments in each of the first display portion, the second display portion, and the third display portion, the step of displaying including disabling one or more segments represented by a second predetermined number of display segments in each of the first display portion, the second display portion, and the third display portion;

wherein the first predetermined number of display segments is a subset of the second predetermined number of display segments;

wherein each display segment that is connected to the failed at least one connector is disabled; and wherein if it is determined that the failure is only related to the third display segment, a modified information is not displayed by the display unit.

2. The method of claim 1 wherein the information for display includes one or more health related values.

3. The method of claim 2 wherein the one or more health related values includes one or more of a measured glucose value, a cholesterol level, and a blood alcohol level.

4. The method of claim 1 wherein the detected failure mode includes one or more of a display unit connector failure, a display unit driver failure, or a display unit connector short.

5. The method of claim 1 further including the step of coupling the display unit to one of an RF receiver unit, an infusion device, or a glucose meter.

6. The method of claim 1 wherein the first predetermined number of segments representing the displayed modified information associated with the detected failure mode is a subset of a combination of display segments representing a numerical value for each of the first display portion, the second display portion, and the third display portion.

7. The method of claim 1 wherein the second predetermined number of display segments represents a numerical value in each of the first display portion, the second display portion, and the third display portion.

8. The method of claim 1 wherein the second predetermined number of display segments in each of the first display portion, the second display portion, and the third display portion represents a glucose value.

9. The method of claim 1 wherein receiving one or more commands to display the information on the display unit includes detecting insertion of an in vitro test strip in a strip port.

10. The method of claim 9 wherein the in vitro test strip includes a blood glucose test strip.

11. The method of claim 1 wherein the display unit includes a seven segment display unit.

12. The method of claim 1 wherein the second predetermined number of display segments includes seven display segments or less in each of the first display portion, the second display portion, and the third display portion, and further, wherein the first predetermined number of display segments includes less than seven display segments in each of the first display portion, the second display portion, and the third display portion.

13. The method of claim 1 wherein the modified information represented by the first predetermined number of display segments includes only a subset of the display segments that represent a numerical value in each of the first display portion, the second display portion, and the third display portion.

14. The method of claim 1 wherein each display segment is connected to a combination of two connectors.

15. The method of claim 14 wherein the combination of two connectors for each display segment is different.

16. An apparatus, comprising:
a display unit;
one or more processors operatively coupled to the display unit, the display unit comprising a first display portion including a first plurality of display segments and a first plurality of connectors, a second display portion including a second plurality of display segments and a second plurality of connectors, and a third display portion including a third plurality of display segments and a third plurality of connectors, wherein each connector is connected to a different combination of two or more display segments in one or more of the first display portion, the second display portion, and the third display portion; and
a memory for storing instructions which, when executed by the one or more processors, causes the one or more processors to display an information on the display unit, to detect a failure mode of the display unit, the failure mode resulting from failure of at least one connector, to determine if the failure is related to one or more of the first display portion, the second display portion, and the third display portion, to disable one or more segments in each of the first display portion, the second display portion, and the third display portion of the information for display represented by a second predetermined number of display segments if it is determined that the failure is related to at least one of the first display portion and the second display portion, and to display a modified information on the display unit indicating the detected failure mode of the display unit, the modified information represented by a first predetermined number of display segments in one or more of the first display portion, the second display portion, and the third display portion, wherein the first predetermined number of display segments is a subset of the second predetermined number of display segments, wherein each display segment that is connected to the failed at least one connector is disabled, and wherein if it is determined that the failure is only related to the third display segment, a modified information is not displayed by the display unit.

17. The apparatus of claim 16 wherein the information for display includes one or more health related values.

18. The apparatus of claim 17 wherein the one or more health related values includes one or more of a measured glucose value, a cholesterol level, and a blood alcohol level.

19. The apparatus of claim 16 wherein the detected failure mode includes one or more of a display unit connector failure, a display unit driver failure, or a display unit connector short.

20. The apparatus of claim 16 wherein the first predetermined number of segments representing the displayed modified information associated with the detected failure mode is a subset of a combination of display segments representing a numerical value in each of the first display portion, the second display portion, and the third display portion.

21. The apparatus of claim 16 wherein the second predetermined number of display segments represents a numerical value in each of the first display portion, the second display portion, and the third display portion.

22. The apparatus of claim 16 wherein the second predetermined number of display segments in each of the first display portion, the second display portion, and the third display portion represents a glucose value.

23. The apparatus of claim 16 further comprising a strip port operatively coupled to the one or more processors, wherein the information for display on the display unit includes information determined from an in vitro test strip in the strip port.

24. The apparatus of claim 23 wherein the in vitro test strip includes a blood glucose test strip.

25. The apparatus of claim 16 wherein the display unit includes a seven segment display unit.

26. The apparatus of claim 16 wherein the second predetermined number of display segments includes seven display segments or less in each of the first display portion, the second display portion, and the third display portion, and further, wherein the first predetermined number of display segments includes less than seven display segments in each of the first display portion, the second display portion, and the third display portion.

27. The apparatus of claim 16 wherein the modified information represented by the first predetermined number of display segments includes only a subset of the display segments that represent a numerical value in each of the first display portion, the second display portion, and the third display portion.

* * * * *